(12) United States Patent
Nakatsuka et al.

(10) Patent No.: US 6,790,877 B2
(45) Date of Patent: Sep. 14, 2004

(54) BONDING COMPOSITIONS FOR DENTAL USE

(75) Inventors: Kazumitsu Nakatsuka, Kurashiki (JP); Koichi Okada, Kurashiki (JP); Satoshi Imazato, Suita (JP); Shigeyuki Ebisu, Toyonaka (JP); Yasuhiko Tsuchitani, Nabari (JP)

(73) Assignee: Kuraray Co., Ltd., Kurashiki (JP)

( * ) Notice: Subject to any disclaimer, the term of this patent is extended or adjusted under 35 U.S.C. 154(b) by 131 days.

(21) Appl. No.: 09/956,552

(22) Filed: Sep. 20, 2001

(65) Prior Publication Data

US 2002/0035169 A1 Mar. 21, 2002

Related U.S. Application Data

(63) Continuation of application No. 09/377,071, filed on Aug. 19, 1999, now Pat. No. 6,355,704.

(30) Foreign Application Priority Data

Aug. 20, 1998 (JP) .......................................... 10-233777
Jan. 27, 1999 (JP) .......................................... 11-017826

(51) Int. Cl.$^7$ ................................................. A61K 6/08
(52) U.S. Cl. ............................ 523/118; 522/8; 522/47; 522/64; 522/112; 522/171; 522/173; 522/182; 522/185; 522/908; 523/109; 523/116; 523/117
(58) Field of Search ............................... 523/109, 116, 523/117, 118; 522/8, 28, 47, 64, 112, 171, 173, 182, 185, 908

(56) References Cited

U.S. PATENT DOCUMENTS

| | | | |
|---|---|---|---|
| 4,719,297 A | | 1/1988 | Henne et al. .................. 522/84 |
| 5,023,107 A | | 6/1991 | Roberts ....................... 523/116 |
| 5,733,949 A | * | 3/1998 | Imazato et al. ............. 523/109 |
| 5,969,000 A | * | 10/1999 | Yang et al. .................. 523/116 |
| 6,051,626 A | * | 4/2000 | Zeng et al. .................. 523/118 |

FOREIGN PATENT DOCUMENTS

| | | |
|---|---|---|
| EP | 0 062 839 | 10/1982 |
| EP | 0 537 774 | 4/1993 |
| EP | 0 705 590 | 4/1996 |
| GB | 2 217 989 | 11/1989 |
| JP | 2-16176 | 1/1990 |
| JP | 3-57916 | 9/1991 |
| WO | WO 96/00559 | 1/1996 |

OTHER PUBLICATIONS

U.S. patent application Ser. No. 10/030,422, filed Jan. 10, 2002, pending.
U.S. patent application Ser. No. 09/956,552, filed Sep. 20, 2001, pending.

* cited by examiner

*Primary Examiner*—Peter Szekely
(74) *Attorney, Agent, or Firm*—Oblon, Spivak, McClelland, Maier & Neustadt, P.C.

(57) ABSTRACT

An antibacterial bonding compositions for dental use, which comprises (A) an antibacterial primer that comprises an antibacterial polymerizable monomer having an ethylenic unsaturated group and at least one or more cationic groups selected from the group consisting of ammonium bases, pyridinium bases and phosphonium bases, and a volatile solvent, and (B) an adhesive composition comprising an acid group having polymerizable monomer, a polymerizable monomer, and a polymerization initiator; and an adhesive compositions for dental use, which comprises (P) an adhesive primer comprising an acid group having polymerizable monomer, a hydrophilic polymerizable monomer, and water, and (Q) a bonding agent comprising a polymerizable monomer, and an acylphosphine oxide compound and an α-diketone compound both serving as a polymerization initiator. The bonding compositions can inhibit the growth of cariogenic bacteria in the bonded area of a tooth as restored with a restorative dental material in dental treatment thereby preventing secondary caries and odontitis around that area, and can enhance the bonding strength, especially the bonding durability of the restorative dental material to the tooth.

10 Claims, No Drawings

BONDING COMPOSITIONS FOR DENTAL USE

This application is a Continuation of application Ser. No. 09/377,071 filed on Aug. 19, 1999 now U.S. Pat. No. 6,355,764.

BACKGROUND OF THE INVENTION

1. Field of the Invention

The present invention relates to bonding compositions suitable for dental use. More precisely, the invention relates to bonding compositions suitable for dental use, which exhibit good adhesiveness between a tooth and restorative dental materials in dental treatment, and which are for preventing the growth of cariogenic bacteria in the bonded area.

2. Description of the Related Art

In dental treatment, where partial defects in teeth are restored through prosthesis with restorative dental materials such as, for example, composite resins, monomers, metal alloys and ceramics for dental restoration, dental bonding compositions are often used. However, when such a restorative dental material is directly bonded to the surface of a tooth, it does not exhibit satisfactory bonding strength since it is not adhesive by itself. As a result, the restorative dental material as directly bonded to a tooth will peel off, or, as the case may be, bacteria will penetrate into the bonded interface between the tooth and the restorative dental material to cause secondary caries and odontitis.

In order to solve this problem, various dental bonding methods which include previous application of some tooth surface treating agents to defective teeth to be restored have heretofore been described. Some reports disclose that such tooth surface treating agents improve the bonding strength between a tooth having been pre-treated with any of them and a restorative dental material applied to the surface-treated tooth. For example, (1) Journal of Dental Research Vol. 34, pp. 849–854, 1955 discloses that some acid etching primers improve the bonding strength of restorative dental materials to tooth enamel; (2) Journal of Dental Research, Vol. 63. pp. 1087–1089, 1984 discloses that a primer composition comprising glutaraldehyde, 2-hydroxyethyl methacrylate (hereinafter referred to as HERA) and water enhances the bonding strength of restorative dental materials to tooth; (3) JP-A-62-223289 discloses that a primer as prepared by adding an acid such as maleic acid, nitric acid or p-toluenesulfonic acid to an aqueous solution of HEMA improves the bonding strength of restorative dental materials to tooth enamel and tooth; (4) JP-A-1-113057 discloses that a primer as prepared by adding a salt of an acid to an aqueous solution of HEMA improves the bonding strength of restorative dental materials to tooth enamel and tooth; and (5) Materials and Instruments for Dental Use, Vol. 9. pp. 65–73, 1990 discloses that a primer as prepared by adding a monomer having an amino acid residue such as N-acryloylaniline or the like to an aqueous solution of HEMA improves the bonding strength of restorative dental materials to tooth enamel and tooth. In addition, (6) JP-A-3-240712 discloses a dental bonding composition as prepared by adding a polymerizable monomer having an acidic group and a curing agent to an aqueous solution of HEMA; and (7) JP-A-4-8368 discloses that adding an amino compound to the dental bonding composition in (6) enhances the ability of the composition to improve the bonding strength of restorative dental materials to teeth.

In particular, a dental bonding method of using a self-etching adhesive primer is an extremely excellent technique, as being easy to perform and provides a high bonding strength to the tooth. The adhesive primer for use in the method comprises an acid (including acidic monomers), a hydrophilic monomer and water, and the method of using it comprises applying the primer to the surface of a tooth and directly applying a bonding material thereto without washing and drying the primer-coated tooth.

However, the self-etching adhesive primer which does not require washing with water is problematic in that the polymerizable monomer will partly remain in the surface layer of tooth even though most of the solvent such as water and the like could be removed through drying with a dental air syringe after its application. The remaining monomer may be polymerized and cured together with the overlaid bonding material by irradiation of light. However, the adhesive primer contains low polymerizable monomers such as hydrophilic monomers and acidic monomers, which could not be polymerized all at once. In order to enhance its polymerizability, some means of improving the adhesive primer have heretofore been tried by adding thereto a photopolymerization initiator, which, however, could not produce the intended effect up to the present. As a result, the polymerization of the monomers in the bonding material (including the adhesive primer) applied to the surface of a tooth is insufficient, and, in a certain period of time after the restoration of the tooth with a restorative dental material, a crevice is formed between the tooth and the butted material to cause marginal leakage, or the butted material is peeled off. Such problems with the adhesive primer have heretofore been often pointed out. In particular, it is said that the problems are remarkable when the bonding material is irradiated by light for a short period of time.

Improving the polymerization curability of the adhesive primer end the bonding material could be attained in some degree by increasing the amount of the photopolymerization initiator in those compositions. Increasing the amount of the initiator too much in those compositions is problematic in that the initiator remaining in the cured products of the compositions will be much released out, since the initiator has no polymerizable group, and, in addition, the mechanical strength of the cured products is lowered and the cured products are discolored with the lapse of time. In that condition, aesthetic tooth crown repairing is impossible. For these reasons, adding too much initiator to the compositions is impracticable.

There is still another problem of secondary caries and odontitis that may be caused by the penetration of bacteria into the bonded interface between tooth and the restorative dental material applied thereto, in addition to the bonding durability failure in the bonding material used. The problem is often pointed out as serious.

For preventing the penetration of bacteria into the bonded interface, antibacterial dental bonding materials have been proposed. For examples JP-A-1-17107 discloses dental cement that contains an antibacterial agent. JP-A-2-16176 and B-198723 disclose a pre-treating agent for dental use that contains a quaternary alkylammonium salt. In these, they do not specifically refer to the antibacterial property of the pre-treating agent, but the quatemaryalkylammonium salt used will have antibacterial ability. However, the antibacterial agent and the quaternary alkylammonium salt have no polymerizable group, and will be therefore released out into the mouth after the dental bonding composition comprising any of them has been polymerized and cured on a tooth. Prior to their dental application, therefore, the antibacterial agent and the quaternary alkylammonium salt require complete safety evaluation. Another problem with them is that the antibacterial agent and the quaternary alkylammonium salt do not exhibit the antibacterial ability for a long period of time.

JP-A-6-9725 and 7-215814 disclose dental compositions containing an antibacterial polymerizable monomer and an acid group-having polymerizable monomer. The antibacterial property as referred to in these is the non-releasing antibacterial property of the polymerized (or cured) products of the dental compositions. Here, the cured products do not release the antibacterial component from them. These publications indicate that the cured products as formed through copolymerization of the antibacterial polymerizable monomer and the other monomer exhibit the antibacterial ability on their surface. Specifically, in the cured polymer products of the dental compositions proposed, the unpolymerized antibacterial compound is exposed out on the surface of the cured polymer, and it may attenuate the bacteria having adhered on the surface of the cured products, but could not kill the bacteria existing in the fine structure of the bonded interface of tooth tubules.

One means of solving the problem has been proposed in JP-A 8-157318, which discloses an antibacterial adhesive primer comprising an antibacterial polymerizable monomer, an acid group-containing polymerizable monomer, an alcoholic hydroxyl group-containing polymerizable monomer, water and a polymerization catalyst.

The technique proposed is characterized in that an antibacterial polymerizable monomer is added to the adhesive primer for killing bacteria in and around teeth while, at the same time, attaining decalcification of teeth, and that the polymerized and cured product of the primer composition exhibits a non-releasing antibacterial ability on its surface. Therefore, this is an extremely useful technique. However, the adhesive primer contains a large amount of slightly-volatile components such as the acid group-containing polymerizable monomer and the alcoholic hydroxyl group-containing polymerizable monomer. Therefore, the probability of contact between bacteria and the antibacterial polymerizable monomer in a resultant product is low, and the adhesive primer could not satisfactorily express the antibacterial ability. In addition, when cured on a tooth the adhesive primer gives a layer of a copolymer of the antibacterial polymerizable monomer and other polymerizable monomers in and around the bonded interface between its cured product and the tooth. However, since the proportion of other polymerizable monomers to the antibacterial monomer is large, the adhesive primer could not still produce a satisfactory antibacterial effect.

Greatly increasing the amount of the antibacterial polymerizable monomer or greatly decreasing the amount of the acid group-containing polymerizable monomer and that of the alcoholic hydroxyl group-containing polymerizable monomer in the adhesive primer could improve the antibacterial ability of the adhesive primer in some degree, which, however, is not practicable as greatly lowering the bonding force of the adhesive primer to a tooth.

A composition comprising an antibacterial polymerizable monomer and a volatile solvent is known. For example, as in JP-A-9-67546, an antibacterial polymerizable monomer may be added to an adhesive composition comprising a monomer capable of bonding to metal and a volatile solvent. However, the adhesive composition disclosed in JP-A-9-67546 is directed to modification of the surface of metal, and nothing is referred to therein that relates to a technique of killing bacteria in and around a tooth. The present inventors tested the compositions of the examples disclosed in JP-A-9-67546, but the compositions did not have high bonding strength to a tooth.

JP-A-10-236915 discloses an antibacterial caries-detecting liquid that comprises an antibacterial polymerizable monomer, a dye, and water and/or a water-miscible solvent. Basically, this liquid is applied to a tooth before the affected tooth is removed from the tooth with a cutting tool, thereby killing the cariogenic bacteria that exist in and around the affected tooth while differentiating the affected-tooth from the non-affected healthy tooth, and the technique disclosed is very useful. However, most of the antibacterial polymerizable monomer in the antibacterial caries-detecting liquid is removed along with the affected tooth which is removed with a cutting tool. In that condition, a high concentration of the monomer could not be in and around the tooth treated with the liquid. Therefore, even though the liquid could kill the cariogenic bacteria existing in and around tooth, it is almost completely ineffective against the cariogenic bacteria that may penetrate into the restored area of a tooth, and therefore could not prevent the growth of the cariogenic bacteria penetrated into that area after treatment.

Accordingly, there remains a need for compositions and methods which overcome the problems described above.

SUMMARY OF THE INVENTION

It is an object of the present invention to provide bonding compositions suitable for dental use.

It us another object of the invention to provide bonding compositions which can inhibit the growth of cariogenic bacteria in the bonded area of a tooth when restored with a restorative dental material, thereby preventing secondary caries and odontitis around that area, and which can enhance the bonding strength, especially the bonding durability of the restorative dental material, to a tooth.

To accomplish the objects noted above, the present inventors have assiduously studied the problem of how to prevent the growth of cariogenic bacteria in the bonded area of tooth as restored with a restorative dental material and of how to entrance the bonding curability of a restorative dental material and a tooth as restored with the material, and, as a result, have discovered the following novel techniques.

Technique for Preventing the Growth of Cariogenic Bacteria

An antibacterial primer comprising a specific antibacterial polymerizable monomer and a volatile solvent is applied around the surface of a tooth, and then dried spontaneously or through dental air blowing so as to make a high concentration of the antibacterial, polymerizable monomer on the tooth surface, thereby killing the bacteria having adhered on the surface of tooth of the tooth. Thereafter, an adhesive composition that comprises an acid group-containing polymerizable monomer, a polymerizable monomer and a polymerization initiator is applied to the area of the tooth, and is cured along with the antibacterial monomer previously applied thereto, thereby forming an antibacterial polymer layer having a high concentration at the interface between the tooth and the bonding material. Bacteria that may penetrate into the bonded interface are killed by the antibacterial polymer layer, and the polymer existing in the bonded interface retains its antibacterial ability for a long period of time.

Technique of Enhancing Bonding Durability of Bonding Compositions

The adhesive composition described above is composed of two compositions, one being an adhesive primer that comprises an acid group-containing polymerizable monomer, a hydrophilic polymerizable monomer and water, and the other being a bonding agent that comprises a polymerizable monomer and a polymerization initiator. The adhesive composition of this type is a so-called self-etching adhesive component. The photopolymerization initiator in the bonding agent contains both an acylphosphine oxide compound and an α-diketone compound. The adhesive primer is first applied to a tooth and is cured along with the bonding agent within a short period of time to form a hard cured layer on the tooth by which the bonding durability of the cured layer to a tooth is enhanced.

Based on the techniques as described above, the present inventors have discovered that the bonding compositions according to the present invention significantly prevent the growth of cariogenic bacteria in the bonded area between tooth and restorative dental material applied thereto and enhance the bonding strength, especially the bonding durability between tooth and a restorative dental material applied thereto, as compared with conventional bonding compositions.

Accordingly, the objects of the invention, and others, may be accomplished with an antibacterial bonding composition suitable for dental use, comprising:

(A) an antibacterial primer comprising (i) an antibacterial polymerizable monomer containing an ethylenic unsaturated group and at least one cationic group selected from the group consisting of ammonium bases, pyridinium bases and phosphonium bases, and (ii) a volatile solvent; and (B) an adhesive composition comprising (i) a first polymerizable monomer containing an acid group, (ii) a second polymerizable monomer, and (iii) a polymerization initiator.

The objects of the invention may also be accomplished with an adhesive composition suitable for dental use, comprising:

(P) an adhesive primer comprising (i) a polymerizable monomer containing an acid group, (ii) a hydrophilic polymerizable monomer, and (iii) water; and (Q) a bonding agent comprising (i) a polymerizable monomer, (ii) an acylphosphine oxide compound, and (iii) an α-diketone compound.

The objects of the invention may also be accomplished with an antibacterial bonding composition suitable for dental use, comprising:

(A) an antibacterial primer comprising (i) an antibacterial polymerizable monomer containing an ethylenic unsaturated group and at least one cationic group selected from the group consisting of ammonium bases, pyridinium bases and phosphonium bases, and (ii) a volatile solvent;

(P) an adhesive primer comprising (i) a polymerizable monomer containing an acid group, (ii) a hydrophilic polymerizable monomer, (iii) water, and (iv) a polymerization initiator; and (Q) a bonding agent comprising a (i) polymerizable monomer, (ii) a polymerizable monomer containing an acid group, (iii) an acylphosphine oxide compound, and (iv) an α-diketone compound, where the ratio of the acylphosphine oxide compound to the α-diketone compound is 1:0.01 to 1:0.5.

The objects of the invention may also be accomplished with a composition suitable for dental use, comprising:

(a) an antibacterial polymerizable monomer containing an ethylenic unsaturated group and at least one cationic group selected from the group consisting of ammonium bases, pyridinium bases and phosphonium bases;

(b) an a polymerizable monomer containing an acid group;

(c) an additional polymerizable monomer; and (d) a polymerization initiator.

The objects of the invention may also be accomplished with a method of providing an antibacterial coating on a tooth, comprising curing the composition described above on the tooth.

The objects of the invention may also be accomplished with a method of applying an antibacterial coating to a tooth, comprising:

applying to a tooth a first composition comprising (i) an antibacterial polymerizable monomer containing an ethylenic unsaturated group and at least one cationic group selected from the group consisting of ammonium bases, pyridinium bases and phosphonium bases, and (ii) a volatile solvent;

removing at least a portion of the volatile solvent;

applying to a tooth a second composition comprising (i) a first polymerizable monomer containing an acid group, (ii) a second polymerizable monomer, and (iii) a polymerization initiator; and then curing the applied compositions.

A more complete appreciation of the invention and many of the attendant advantages thereof will be readily obtained as the same becomes better understood by reference to the following detailed description.

DETAILED DESCRIPTION OF THE INVENTION

The term "adhesive composition" as used herein refers to an adhesive for bonding a restorative dental material to a tooth, and this includes an adhesive primer that is applied to a tooth or to a restorative dental material prior to bonding the tooth and the material so as to enhance the bonding strength between the two. Specifically, the adhesive compositions in the invention encompasses any combination of two or more compositions that may be wrapped or packaged separately, for example, a combination of an adhesive primer and a bonding agent, or a combination of an adhesive primer and a resin cement.

The antibacterial polymerizable monomer for use in the invention has an ethylenic unsaturated group and at least one cationic group selected from the group consisting of ammonium bases, pyridinium bases and phosphonium bases. For example, generally used are antibacterial polymerizable monomers of the following general formulae (I) to (IV):

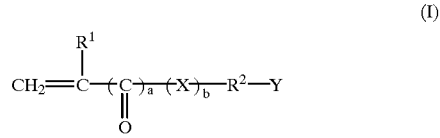

(I)

wherein $R^1$=H or $CH_3$, $R^2$=alkylene group having 2–25 carbon atoms,

X=O, S, NH,

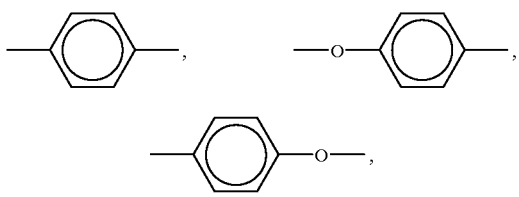

—CH₂O— or —OCH₂—, a=0 or 1,
b=0 or 1,

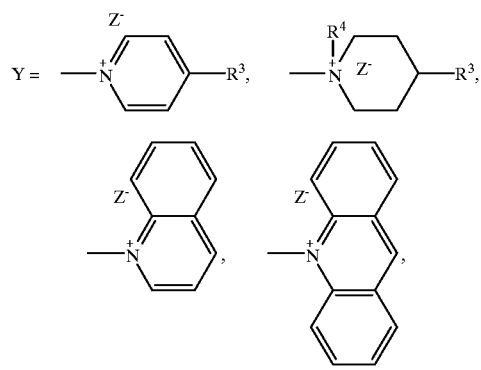

$R^3$=H or —(V)$_c$—$R^7$—W,
$R^4$, $R^5$, $R^6$=(V)$_c$—$R^7$—W,
V=O, S, NH,

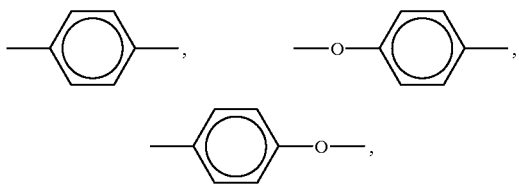

—CH₂O— or —OCH₂—, $R^7$=alkylene group having 1–25 carbon atoms,
W=H, CH₃, OH or

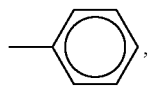

c=0 or 1,
Z=anion.

$$\left( CH_2 = \overset{R^8}{\underset{}{C}} - \underset{\underset{O}{\|}}{(C)}_d - (X)_e - R^9 \right)_2 Y^1 \quad (II)$$

wherein $R^8$=H or CH₃,
$R^9$=alkylene group having 2–25 carbon atoms,
X=O, S, NH,

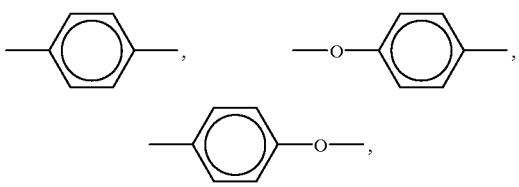

—CH₂O— or —OCH₂—, d=0 or 1,
e=0 or 1,

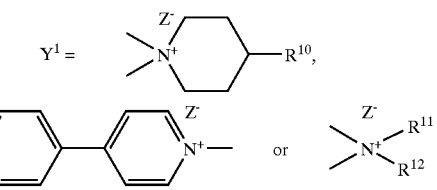

$R^{10}$=H or —(V)$_f$—$R^{13}$—W,
$R^{11}$, $R^{12}$=(V)$_f$—$R^{13}$—W,
V=O, S, NH

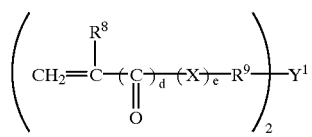

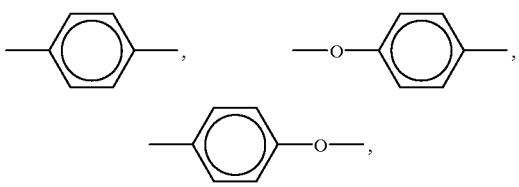

—CH₂O— or —OCH₂—, $R^{13}$=alkylene group having 1–25 carbon atoms,
W=H, CH₃, OH or

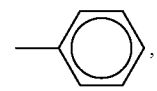

f=0 or 1,
Z=anion.

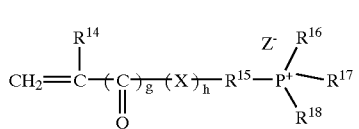
(III)

wherein
$R^{14}$=H or $CH_3$,
$R^{15}$=alkylene group having 2–25 carbon atoms,
X=O, S, NH,

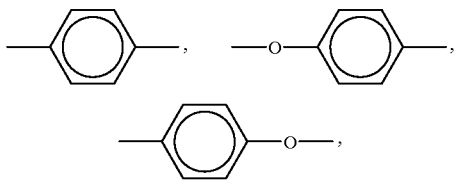

—$CH_2O$— or —$OCH_2$—,
g=0 or 1,
h=0 or 1,
$R^{16}$, $R^{17}$, $R^{18}$=$(V)_1$—$R^{19}$—W,
V=O, S, NH,

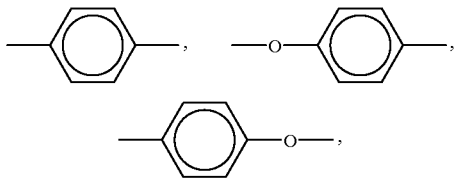

—$CH_2O$— or —$OCH_2$—,
$R^{19}$=alkylene group having 1–25 carbon atoms,
W=H, $CH_3$, OH or

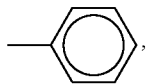

i=0 or 1,
Z=anion.

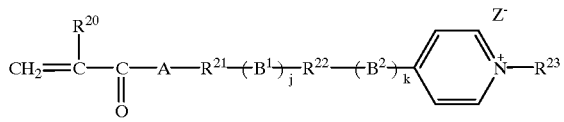
(IV)

wherein
$R^{20}$=H or $CH_3$,
$R^{21}$, $R^{22}$=alkylene group having 1–25 carbon atoms,
j=0 or 1, k=0 or 1,
A=O, S, NH,

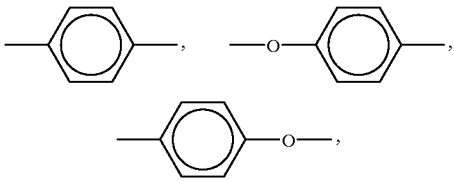

—$CH_2O$— or —$OCH_2$—,
$B^1$, $B^2$,=—CO—, —COO—, —OCO—, —O—, —S—,
—NHCOO— or —OCONH—,
$R^{23}$=—$(V)_p$—$R^{24}$W',
V=O, S, NH,

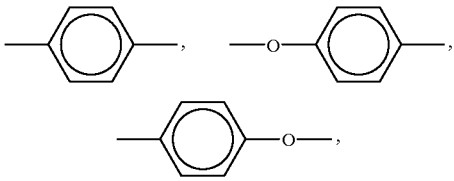

—$CH_2O$— or —$OCH_2$—,
$R^{24}$=alkylene group having 1–25 carbon atoms,
$W^1$=H, $CH_3$, OH,

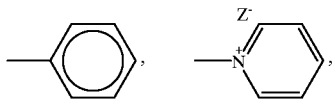

p=0 or 1,
Z=anion.

Specific examples of the compounds of formula (I) include the following:

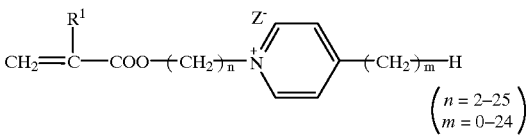
$\begin{pmatrix} n = 2-25 \\ m = 0-24 \end{pmatrix}$

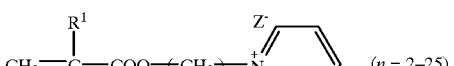
(n = 2–25)

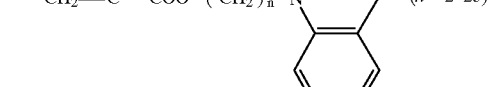
(n = 2–25)

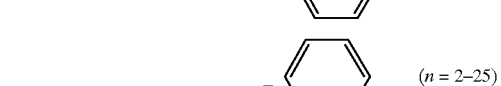
(n = 2–25)

-continued

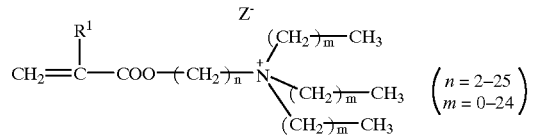

$\begin{pmatrix} n = 2\text{--}25 \\ m = 0\text{--}24 \end{pmatrix}$

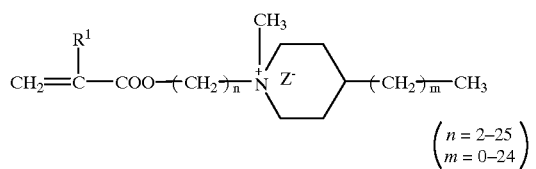

$\begin{pmatrix} n = 2\text{--}25 \\ m = 0\text{--}24 \end{pmatrix}$

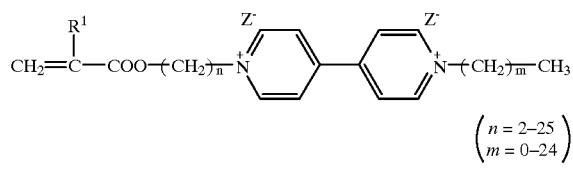

$\begin{pmatrix} n = 2\text{--}25 \\ m = 0\text{--}24 \end{pmatrix}$ $R^1$ = H, $CH_3$
Z = F, Cl, Br, I, 1/2 $PO_4$, 1/2 $SO_4$, $CH_3$—$SO_3$, $CH_3COO$,

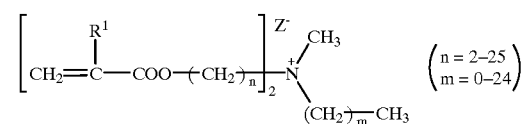

Specific examples of the compounds of formula (II) include the following:

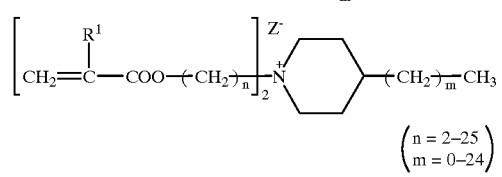

$\begin{pmatrix} n = 2\text{--}25 \\ m = 0\text{--}24 \end{pmatrix}$

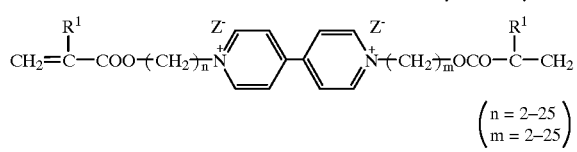

$\begin{pmatrix} n = 2\text{--}25 \\ m = 2\text{--}25 \end{pmatrix}$

-continued

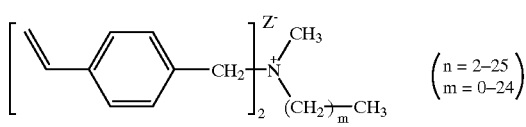

$\begin{pmatrix} n = 2\text{--}25 \\ m = 0\text{--}24 \end{pmatrix}$ $R^1$ = H, $CH_3$
Z = F, Cl, Br, I, 1/2 $PO_4$, 1/2 $SO_4$, $CH_3$—$SO_3$, $CH_3COO$,

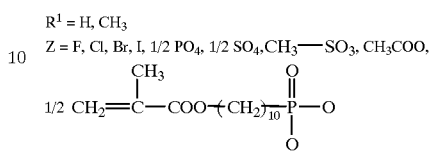

Specific examples of the compounds of formula (III) include the following:

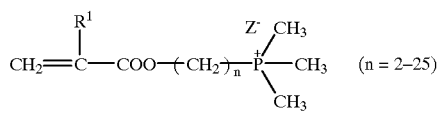  (n = 2–25)

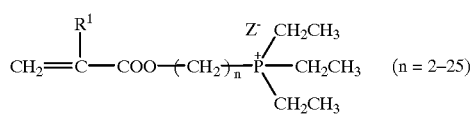  (n = 2–25)

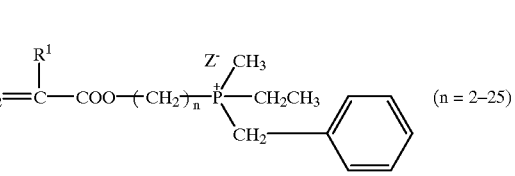  (n = 2–25)

$R^1$ = H, $CH_3$
Z = F, Cl, Br, I, 1/2 $PO_4$, 1/2 $SO_4$, $CH_3$—$SO_3$, $CH_3COO$,

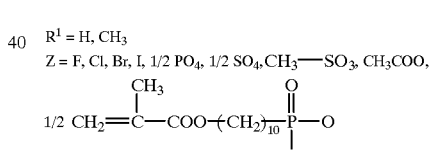

Specific examples of the compounds of formula (IV) include the following:

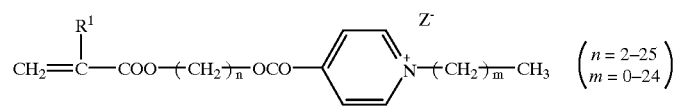  $\begin{pmatrix} n = 2\text{--}25 \\ m = 0\text{--}24 \end{pmatrix}$

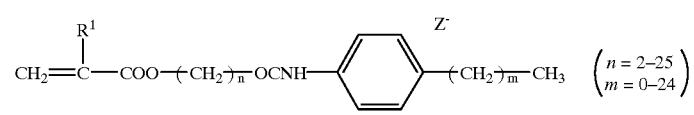  $\begin{pmatrix} n = 2\text{--}25 \\ m = 0\text{--}24 \end{pmatrix}$

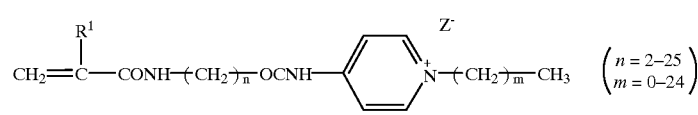  $\begin{pmatrix} n = 2\text{--}25 \\ m = 0\text{--}24 \end{pmatrix}$ -continued

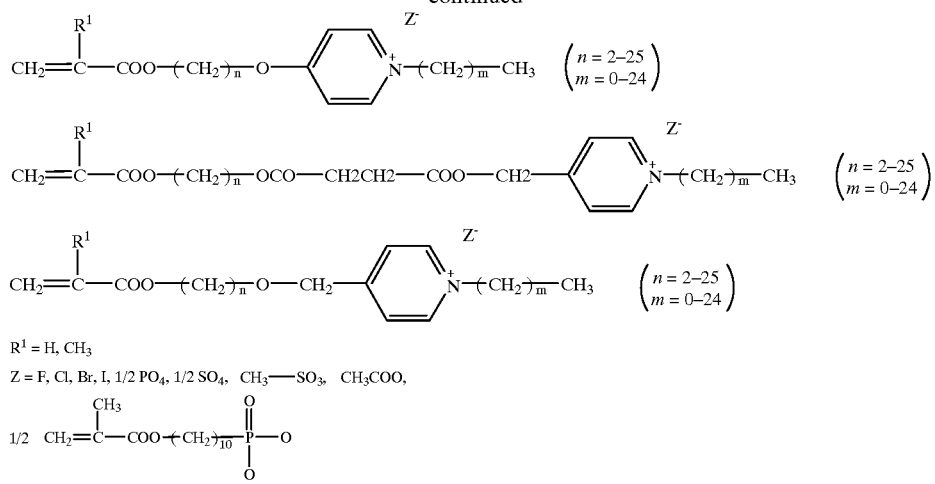

R¹ = H, CH₃

Z = F, Cl, Br, I, 1/2 PO₄, 1/2 SO₄, CH₃—SO₃, CH₃COO, $$1/2 \quad CH_2=\overset{CH_3}{\underset{|}{C}}-COO-(CH_2)_{\overline{10}}-\overset{O}{\underset{\underset{O}{|}}{\overset{\|}{P}}}-O$$

Among these monomers, preferred are the antibacterial polymerizable monomers having an alkylene group with 10 or more carbon atoms, which exhibit good antibacterial properties. Such monomers include, for example, methacryloyloxydodecylpyridinium salts, methacryloyloxyhexadecylpyridinium salts, methacryloyloxydecyltriethylammonium salts, 4-hexadecylmethacryloyloxyethylpyridinium salts, methacryloylaxyethylhexadecylbipyridinium salts, methacryloyloxydodecyltrimethylphosphonium salts, methacryloyloxyoctadecyltriethylphosphonium salts, 4-methacryloyloxyethyldodecylpyrldinium salts, di(4-vinylbenzyl) hexadecylmethylammonium salts, di(methacryloyloxyethyl)dodecylmethylammonium salts, methacryloyloxyethyl(4-N-hexadecylpyridinylmethyl) succinate halides, etc.

In the antibacterial polymerizable monomers, the anions which are formally paired with the ammonium cation, the pyridinium cation and the phosphonium cation are not particularly limited. They include, for example, halides such as $F^-$, $Cl^-$, $Br^-$, $I^-$; anions derived from inorganic acids such as $PO_4^{3-}$, $HPO_3^{2-}$, $H_2PO_4^-$, $Na_2PO_3^{2-}$, $Na_2PO_3^-$, $SO_4^{2-}$, $HSO_4^-$, $KSO_4^-$, $NO_3^-$ etc.; anions derived from organic acids such as methanesulfonic acid, acetic acid, propionic acid, benzoic acid, phenol, p-toluenesulfonic acid, maleic acid, oxalic acid, citric acid, etc.; and also anions derived from polymerizable acidic compounds that will be mentioned hereinunder. They further include anions derived from polymerizable acids such as $AlF_6^{3-}$, $AsFe^-$, $BF_4^-$, $BiCl_4^{2-}$, $BiCl_3^{2-}$, $SbCl_6^-$, $SbF_6^-$, $PF_6^-$, $GaCl_4^-$, $InF_4^-$, $TiF_6^{2-}$, $ZrF_6^-$, $FeCl_4^-$, $SnCl_6^-$, etc. Halides are the preferred anions. These anions are paired with the cations, either singly or as combined.

One or more antibacterial polymerizable monomers may be used herein either singly or as combined, i.e., as a mixture. The amount of the antibacterial polymerizable monomer in the antibacterial primer may generally fall between 0.000001% by weight and 50% by weight, preferably between 0.001% by weight and 30% by weight, more preferably between 0.01% by weight and 10% by weight, based on the total weight of the primer. These ranges include all specific values and subranges therebetween, such as 0.0001, 0.01, 0.1, 0.5, 1, 2, 5, 15, 20 and 25% by weight, based on the total weight of the primer. The ranges described above, and those described below, include the endpoints unless noted otherwise.

In the present invention, the volatile solvent in the antibacterial primer has the ability to dissolve the antibacterial polymerizable monomer. The solvent includes, for example, volatile organic solvents having a boiling point at ordinary pressure of not higher than 250° C., water, and mixtures thereof. Examples of volatile organic solvents include alcohols such as methanol, ethanol, 2-ethylbutanol isopropanol; ketones such as acetone, methylethyl ketone, 2-butanone, 3-pentanone; ethers such as diethyl tetrahydrofuran; as well as ethyl acetate, toluene, xylene, p-cymene, hexane, octane, pentane, methylene chloride, 1,2-dichloroethane, methyl methacrylate.

Of those, preferred are volatile organic solvents having a boiling point at ordinary pressure of not higher than 100° C., such as ethanol, acetone. One or more of those solvents may be used either singly or in combination, i.e., solvent mixtures may be used.

The amount of the solvent in the antibacterial primer may generally fall between 50% by weight and 99.999999% by weight, preferably between 70% by weight and 99.9999% by weight, more preferably between 90% by weight and 99.99% by weight, based on the total weight of the primer. These ranges include all specific values and subranges therebetween, such as 60, 75, 80, 85, 90, 95, 99, and 99.9% by weight, based on the total weight of the primer.

In some embodiments, it is often desirable to add polymerization initiator to the antibacterial primer which comprises an antibacterial polymerizable monomer and a volatile solvent such as those noted above, for the purpose of more firmly curing the antibacterial polymerizable monomer. The polymerization initiator is not specifically limited, and may be any inhibitor well-known to those skilled in the art.

Photopolymerization initiators may be used, including, for example, α-diketone/reducing agent, ketal/reducing agent, thioxanthone/reducing agent, etc. Examples of the α-diketone include camphorquinone, benzil, 2,3-pentanedione, etc. Examples of the ketal include benzyldimethyl ketal, benzyldiethyl ketal, etc. Examples of the thioxanthone include 2-chlorothioxanthone, 2,4-diethylthioxanthone, etc. Examples of the reducing agent include tertiary amines such as 2-(dimethylamino)ethyl methacrylate, N,N-bis[(meth)acryloyloxyethyl]-N-methylamine, ethyl 4-dimethylaminobenzoate, butyl 4-dimethylaminobenzoate, butoxyethyl 4-dimethylaminobenzoate, N-methyldiethanolamine, 4-dimethylaminobenzophenone, dimethylaminophenanthol, etc., aldehydes such as dimethylaminobenzaldehyde, terephthalaldehyde, etc.; thiol group-having compounds such as 2-mercaptobenzoxazole, decanethiol, 3-mercaptopropyltrimethoxysilane, thiobenzoic acids etc. For photopolymerization through UV exposure, preferable examples include benzoin alkyl ethers, benzyldimethyl ketal, etc.

Also preferably used are acylphosphine oxide compounds, which include, for example, 2,4,6-trimethylbenzoyldiphenylphosphine oxide, 2,6-dimethoxybenzoyldiphenylphosphine oxide, 2,6-dichlorobenzoyldiphenylphosphine oxide, 2,3,5,6-tetramethylbenzoyldiphenylphosphine oxide, benzoyldi-(2,6-dimethylphenyl) phosphonate, 2,4,6-trimethylbenzoylethoxyphenylphosphine oxide, as well as water-soluble acylphosphine oxides such as those disclosed in JP-B-3-57916. These acylphosphine oxide compounds may be used either singly or as combined with a reducing agent of, for example, various amines, aldehydes, mercaptans, salts of sulfinic acids, etc.

One or more of these photopolymerization initiators and reducing agents may be used herein, i.e., mixtures may be used. The amount of the photopolymerization initiator and the reducing agent in the antibacterial primer may generally fall between 0.01% by weight and 20% by weight, preferably between 0.01% by weight and 10% by weight, more preferably between 0.1% by weight and 5% by weights based on the total weight of the antibacterial primer. These ranges include all specific values and subranges therebetween, such as 0.02, 0.05, 1, 2, 5, 10 and 15% by weight, based on the total weight of the antibacterial primer.

Chemical polymerization initiators are also employable herein, which are preferably redox polymerization initiators. Where such a redox polymerization initiator is used for the antibacterial primer which constitutes the bonding composition of the invention, the antibacterial primer should be divided into at least two parts which are separately wrapped or packaged and which separately contain either one of the oxidizing agent and the reducing agent for the initiator. However, in practical use of the antibacterial bonding composition of the invention, the antibacterial primer shall be all the time combined with the other constituent component of the adhesive component. Therefore, in the composition, the oxidizing agent and the reducing agent for the initiator may be separately incorporated into the antibacterial primer and the adhesive component.

The oxidizing agent may be an organic peroxide, including, for example, diacyl peroxides, peroxy esters, dialkyl peroxides, peroxy ketals, ketone peroxides, hydroperoxides, etc. Specific examples of the diacyl peroxides include benzoyl peroxide, 2,4-dichlorobenzoyl peroxide, m-toluoyl peroxide, etc.

The peroxy esters include, for example, t-butylperoxy benzoate, bis-t-butylperoxy isophthalate, 2,5-dimethy-2,5-bis(benzoylperoxy)hexane, t-butylperoxy 2-ethylhexanoate, t-butylperoxyisopropyl carbonate, etc.

The dialkyl peroxides include, for example, dicumyl peroxide, di-t-butyl peroxide, lauroyl peroxide, etc.

The peroxy ketals include, for example, 1,1-bis(t-butylperoxy)-3,3,5-trimethylcyclohexane, 2,2-bis(t-butylperoxy)butane, 1,1-bis(t-butylperoxy)cyclohexane, etc.

The ketone peroxides include, for example, methyl ethyl ketone peroxide, cyclohexanone peroxide, methyl acetacetate peroxide, etc.

The hydroperoxides include, for example, t-butylhydroperoxide, cumenehydroperoxide, p-diisopropylbenzeneperoxide, etc. One or more these oxidizing agents may be used either singly or as combined.

As the reducing agent, preferred are aromatic tertiary amine, aliphatic tertiary amines, as well as sulfinic acids, and salts thereof.

The aromatic tertiary amines include, for example, N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-methylaniline, N,N-dimethyl-4-ethylaniline, N,N-dimethyl-4-t-propylaniline, N,N-dimethyl-4-t-butylaniline, N,N-dimethyl-3,5-di-t-butylaniline, N,N-di(2-hydroxyethyl)-p-toluidine, N,N-di(2 hydroxyethyl)-3,5-dimethylaniline, N,N-di(2-hydroxyethyl)-3,4-diethylaniline, N,N-di(2-hydroxyethyl)-4-ethylaniline, N,N-di(2-hydroxyethyl)-4-i-propylaniline, N,N-di(2-hydroxyethyl)-4-t-butylaniline, N,N-di(2-hydroxyethyl)3,5-di-i-propylaniline, N,N-bis(2-hydroxyethyl)-3,5-di-t-butylaniline, ethyl 4-dimethylamonobenzoate, n-butoxyethyl 4-dimethylaminobenzoate, (2-methacryloyloxy)ethyl, 4-dimethylaminobenzoate, etc.

The aliphatic tertiary amines include, for example, trimethylamine, triethylamine, N-methyldiethanolamine, N-ethyldiethanolamine, N-n-butyldiethanolamine, N-lauryldiethanolamine, triethanolamine, (2-dimethylamino)ethyl methacrylate, N-methyldiethanolamine dimethacrylate, N-ethyldiethanolamine dimethacrylate, triethanolamine monomethacrylate, triethanolamine dimethacrylate, triethanolamine trimethacrylate, etc.

The sulfinic acids end their salts include, for example, benzenesulfinic acid, sodium benzenesulfinate, potassium benzenesulfinate, calcium benzenesulfinate, lithium benzenesulfinate, toluenesulfinic acid, sodium toluenesulfinate, potassium toluenesulfinate, calcium toluenesulfinate, lithium toluenesulfinate, 2,4,6-trimethylbenzenesulfinic acid, sodium 2,4,6-trimethylbenzenesulfinate, potassium 2,4,6-trimethylbenzenesulfinate, calcium 2,4,6-trimethylbenzenesulfinate, lithium 2,4,6-trimethylbenzenesulfinate, 2,4,6-triethylbenzenesulfinic acid, sodium 2,4,6-riethylbenzenesulfinate, potassium 2,4,6-triethylbenzenesulfinate, calcium 2,4,6-triethylbenzenesulfinate, 2,4,6-i-propylbenzenesulfinic acid, sodium 2,4,6-i-propylbenzenesulfinate, potassium 2,4,6-propylbenzenesulfinate, calcium 2,4,6-i-propylbenzenesulfinate, etc.

One or more of these reducing agents may be used either singly or in combination.

The amount of the oxidizing agent and the reducing agent in the bonding composition of the invention may generally fall between 0.0001% by weight and 20% by weight, preferably between 0.01% by weight and 10% by weight, more preferably between 0.1% by weight and 5% by weight, based on the total weight of the antibacterial primer that constitutes the compositions. These ranges include all specific values and subranges therebetween, including 0.001, 0.2, 0.5, 1, 2, 10 and 15% by weight, based on the total weight of the antibacterial primer.

The antibacterial primer of the invention may optionally contain inorganic acids such as phosphoric acid, nitric acid, etc., organic acids such as maleic acid, citric acid etc., as well as polymerization inhibitors, antioxidants, UV absorbents, pigments, dyes and other additives, in addition to the components described above. Any additional polymerizable monomer may also be incorporated into the antibacterial primer, so long as it does not significantly interfere with the antibacterial capabilities of the primer. The amount of the additional polymerizable monomer, if any, in the antibacterial primer is generally at most 30% by weight, preferably at most 10% by weight, based on the total weight of the antibacterial primer. A fluorine compound having anticarious capabilities, such as sodium fluoride, may also be incorporated in the primer.

The antibacterial primer of the invention may also contain a filler. The filler may be any of organic, inorganic or even composite fillers. The inorganic fillers include, for example, silica, silica-based minerals such as kaolin, clay, mica, eta.; and silica-based ceramics and glass additionally containing any of $Al_2O_3$, $B_2O_3$, $TiO_2$, $ZrO_2$, BaO, $La_2O_3$, $SrO_2$, CaO, $P_2O_5$, etc. Especially preferred are lanthanum glass, barium glass, strontium glass, soda glass, lithium borosilicate glass, zinc glass, fluoroaluminium borosilicate glass, borosilicate glass, bioglass, etc. Also preferred are crystalline quartz, hydroxyapatite, alumina, titanium oxide, yttrium oxide, zirconia, calcium phosphate, barium sulfate, aluminium hydroxide, etc.

The organic fillers may be an organic resin, including, for example, polymethyl methacrylate, polymers of polyfunctional methacrylates, polyamides, polystyrenes, polyvinyl chloride, chloroprene rubber, nitrile rubber, styrene-butadiene rubber, etc.

Also useful herein are inorganic/organic composite fillers, which may be prepared by dispersing an inorganic filler in an organic resin, or by coating an inorganic filler with an organic resin.

If desired, the fillers may be previously subjected to surface treatment with any known surface-treating agent such as a silane coupling agent or the like. The surface-treated fillers are effective for controlling the fluidity of the antibacterial primer and for enhancing the dispersibility thereof. The surface-treating agent includes, for example, vinyltrimethoxysilane, vinyltriethoxysilane, vinyltrichlorosilane, vinyltri(β-methoxyethoxy)silane, γ-methacryloyloxypropyltrimethoxysilane, γ-glycidoxypropyl-trimethoxysilane, γ-mercaptopropyl-trimethoxysilane, and aminopropyltriethoxysilane.

One or more those fillers may be used either singly or as combined. The amount of the filler, if any, in the antibacterial primer is generally at most 30% by weight, preferably at most 10% by weight, based on the total weight of the primer. As the filler, more preferred is colloidal silica having a mean particle size of at most 0.1 μm.

The acid group-containing polymerizable monomer in the adhesive composition of the invention is a polymerizable monomer which contains at least one acid group. For example, the acid group may be a phosphoric acid residue, a pyrophosphorio acid residue, a thiophosphoric acid residue, a carboxylio acid residue, a sulfonic acid residue or the like, and has a polymerizable unsaturated group of, for example, an acryloyl group, a methacryloyl group, a vinyl group, a styrene group or the like. Specific examples of the monomer are described below. The terminology "(meth) acryl" as used herein includes both "methacryl" and "acryl".

The polymerizable monomers having a phosphoric acid residue include, for example, 2-(meth)acryloyloxyethyl dihydrogenphosphate, 4-(meth)acryloyloxybutyl dithydrogenphosphate, 6-(meth)acryloyloxyhexyl dihydrogenphosphate, 8-(meth)acryloyloxyoctyl 9-(meth) acryloyloxynonyl dihydrogenphosphate, 10-(meth) acryloyloxydecyl dihydrogenphosphate, 11-(meth) acryloyloxyundecyl dihydrogenphosphate, 20-(meth) acryloyloxyeicosyl dihydrogenphosphate, 1,3-di(meth) acryloyloxypropyl-2-dihydrogenphosphate, dihydrogenghosphate, 2-(meth)acryloyloxyethylphenyl phosphate, 2-(meth)acryloyloxyethyl-2'-bromoethyl phosphate, (meth)acryloyloxyethylphenyl phosohonate, and their acid chlorides.

The polymerizable monomers having a pyrophosphine acid residue include, for example, di(2-(meth) acryloyloxyethyl) pyrophosphate, di(2-(meth) acryloyloxybutyl) pyrophosphate, di(2-(meth) acryloyloxybexyl) pyrophosphate, di(2-(meth) acryloyloxydecyl) pyrophosphates, and their acid chlorides.

The polymerizable monomers having a thiophosphoric acid residue include, for example, 2-(meth)acryloyloxyethyl dihydrogendithiophosphate, 10-(meth)acryloyloxydecyl dihydrogendithiophosphate, and their acid chlorides.

The polymerizable monomers having a carboxylic acid residue include, for example, maleic acid, maleic anhydride, 4-(meth)acryloyloxyethoxycarbonylphthalic acid, 4-(meth) acryloyloxyethoxycarbonylphthalic anhydride, 5-(meth) acryloylaminopentylcarboxylic acid, 11-(meth)aryloyloxy-1,1-undecanedicarboxylic acid, and their acid chlorides.

The polymerizable monomers having a sulfonic acid residue may be compounds having a sulfonic acid group, such as, for example, 2-(meth)acrylamido-2-methylpropanesulfonic acid, styrenesulfonic acid, 2-sulfoethyl(meth)acrylate, etc.

One or more those acid group-containing polymerizable monomers may be used herein either singly or in combination, i.e., mixtures of different acid group-containing monomers may be used.

The amount of the acid group-containing polymerizable monomer in the adhesive component may generally fall between 0.1% by weight and 80% by weight, preferably between 1% by weight and 60% by weight, based on the total weight of the adhesive composition. These ranges include all specific values and subranges therebetween, such as 0.02, 0.05, 2, 5, 10, 25, 50 and 75% by weight, based on the total weight of the adhesive composition.

Examples of the other polymerizable monomer which is also in the adhesive composition include, esters of α-cyanoacrylic acid, (meth)acrylic acid, α-halogenoacrylic acids, crotonic acid, cinnamic acid, sorbic acid, maleic acid, itaconic acid and the like; as well as (meth)acrylamide, (meth)acrylamide derivatives, vinyl esters, vinyl ethers, mono-N-vinyl derivatives, styrene derivatives, etc. Of those, (meth)acrylates are preferred. Examples of the polymerizable monomers are described below.

The terminology "monofunctional monomer" as referred to herein means to indicate a monomer haying one olefinic double bond.

(i) Monofunctional Monomers

These include, for example, methyl (methacrylate, iso-butyl (meth)acrylate, benzyl (meth)acrylate, lauryl (meth) acrylate, 2-(N,N-dimethylamino)ethyl (meth)acrylate, 2,3-dibromopropyl (meth)acrylate, 3-methacryloyloxypropyl-trimethoxysilane, 2-hydroxyethyl (meth)acrylate, 6-hydroxyhexyl (meth)acrylate, 10-hydroxydecyl (meth) acrylate, propylene glycol mono(meth)acrylate, glycerin mono(meth)acrylate, erythritol mono(meth)acrylate, N-methylol(meth)acrylamide, N-hydroxyethyl(meth) acrylamide, N,N-(dibydroxyethyl)(meth)acrylamide, (meth) acryloylaxydodecylpyridinium bromide, (meth) acryloyloxydodecylpyridinium chloride, (meth) acryloyloxyhexdodecylpyridinium bromide, (meth) acryloyloxyhexdodecylpyridinium chloride.

(ii) Difunctional Monomers

These include, for example, ethylene glycol di(meth) acrylate, triethylene glycol di(meth)acrylate, polyethylene glycol di(meth)acrylate, propylene glycol di(meth)acrylate, neopentyl glycol di(meth)acrylate, 1,6-hexanediol di(meth)acrylate, 1,10-decanediol di(meth)acrylate, bisphenol A diglycidyl(meth)acrylate, 2,2-bis[4-(meth)acryloyloyethoxyphenyl]propane, 2,2-bis[4-(meth)acryloyloxypolyethoxyphenyl]propane, 2,2-bis[4-[3-(meth)acryloyloxy-2-hydroxypropoxy]phenyl]propane, 1,2-bis[3-(meth)acryloyloxy-2-hydroxypropoxy]ethane, pentaerythritol di(meth)acrylate, 1,2-bis(3-methacryloyloxy-2-hydroxypropoxy)ethane, [2,2,4-trimethylhexamethylenebis(2-carbamoyloxyethyl)] dimethacrylate.

(iii) Trifunctional or Higher Polyfunctional Monomers

They include, for example, trimethylolpropane tri(meth)acrylate, trimethylolethane tri(meth)acrylate, tetramethylolmethane tri(meth)acrylate, pentaerythritol tetra(meth)acrylate, N,N'-(2,2,4, trimethylhexamethylene)bis[2-(aminocarboxy)propane-1,3-diol] tetramethacrylate, 1,7-diacryloyloxy-2,2,6,6-tetracryloyloxymethyl-4-hydroxyheptane.

One or more of these polymerizable monomers may be used either singly or in combination.

The amount of the polymerizable monomer in the adhesive composition may generally fall between 5 and 95% by weight, preferably between 30 and 90% by weight, more preferably between 40 and 80% by weight, based on the total weight of the adhesive component. These ranges include all specific values and subranges therebetween, such as 10, 15, 20, 25, 50, 75 and 90% by weight, based on the total weight of the adhesive component.

The polymerization initiator in the adhesive composition is important for curing both the adhesive component and the antibacterial primer, and is not particularly limited. Any of the well-known polymerization initiators known may be used in the present invention. The polymerization initiator may be any of the well-known photopolymerization initiators and/or chemical polymerization initiators.

For the photopolymerization initiators usable in the adhesive component, examples include those described above for the antibacterial primer. The same initiator in the antibacterial primer mentioned hereinabove may also be in the adhesive component. Especially preferred for the adhesive component is a combination of α-diketone/acylphosphine oxide/reducing agent.

One or more photopolymerization initiators and also reducing agents may be used either singly or as combined. The amount of the photopolymerization initiator and the reducing agent in the adhesive composition may generally fall between 0.01 and 20% by weight, preferably between 0.1 and 5% by weight, based on the total weight of the adhesive composition. These ranges include all specific values and subranges therebetween, such as 0.02, 0.05, 0.2, 0.5, 1, 2, 8, 10 and 15% by weight, based on the total weight of the adhesive composition.

When the adhesive composition of the invention will be exposed to the ambient light, the composition should be protected from being thickened, gelled or cured owing to the ambient light within a short period of time. For this purpose, it is desirable that the total amount of the acylphosphine oxide compound and the α-diketone compound is limited to fall between 1% by weight and 6% by weight. More preferably, the ratio of the acylphosphine oxide compound to the α-diketone compound in the adhesive composition is so defined that the latter is from 0.01 parts by weight to 0.5 parts by weight based on one part by weight of the former. In the ratio defined above, the adhesive composition is stable even in the ambient light and its photocurability is high.

Chemical polymerization initiators are also employable herein, which are preferably redox polymerization initiators. Where such a redox polymerization initiator is used for the adhesive composition, the adhesive composition must be divided into at least two parts which are separately wrapped or packaged and which separately contain either one of the oxidizing agent and the reducing agent for the initiator. However, where the adhesive composition is combined with the antibacterial primer described above to constitute the antibacterial bonding compositions of the invention, any one of the oxidizing agent and the reducing agent for the initiator may be incorporated in either the antibacterial primer or the adhesive composition. In that case, the adhesive composition may be in the form of a single package.

For the oxidizing agents and the reducing agents usable in the adhesive composition, examples include those described above for the antibacterial primer. The same initiator in the antibacterial primer may also be in the adhesive composition.

One or more oxidizing agents and reducing agents may be used either singly or as combined. The amount of the oxidizing agent and the reducing agent to be in the adhesive component may generally fall between 0.01 and 20% by weight, preferably between 0.1 and 10% by weight, based on the total weight of the adhesive composition. These ranges include all specific values and subranges therebetween, such as 0.02, 0.05, 0.2, 0.5, 1, 2, 5 and 15% by weight, based on the total weight of the adhesive composition.

The adhesive composition in the invention optionally contain a filler, which is for improving the handlability, the coatability and the mechanical strength of the composition. For examples of the filler, referred to are those of inorganic fillers, organic fillers, inorganic/organic composite fillers mentioned hereinabove for the antibacterial primer. The same filler as in the antibacterial primer mentioned hereinabove could also be in the adhesive composition.

One or more such fillers may be used either singly or as combined. The amount of the filler, if any, in the adhesive composition is generally at most 70% by weight, preferably at most 50% by weight, based on the total weight of the adhesive composition. Where the adhesive composition contains an organic solvent or water, the amount of the filler therein is preferably at most 30% by weight. As the filler, especially preferred is colloidal silica having a mean particle size of at most 0.1 μm.

The adhesive composition in the invention may optionally contain polymerization inhibitors, antioxidants, UV absorbents, pigments dyes and other additives in addition to the ingredients noted above. A fluorine compound having anticarious capabilities, such as sodium fluoride, may be incorporated in the adhesive composition.

Preferably, the adhesive composition of the present invention is divided into plural parts, for example, as a combination of an adhesive primer and a bonding agent, or a combination of an adhesive primer and a resin cement. The adhesive composition that is in the form of such combinations is preferred, because its bonding strength to tooth is greatly increased. More preferably, the divided parts of the adhesive composition selectively contain specific ingredients, as mentioned below.

(A) Adhesive Primer

Preferably, the adhesive primer comprises an acid group containing polymerizable monomer such as those described above (in an amount of from 5% by weight to 50% by weight), a hydrophilic polymerizable monomer having a solubility in water at 25° C. of at least 5% (in an amount of from 20% by weight to 95% by weight), and water (in an amount of from 5% by weight to 70% by weight). Comprising these components, the adhesive primer exhibits improved penetrability into teeth and also improved adhesiveness to teeth.

More preferably, the adhesive primer also contains a polymerization initiator (in an amount of from 0.1 to 5% by weight).

For specific examples of the constituent ingredients in the adhesive primer, examples include those described above. In particular, as the hydrophilic polymerizable monomer, preferred are 2-hydroxyethyl methacrylate, 3-hydroxypropoylmethacrylate, polyethylene glycol dimethacrylate in which the number of oxyethylene groups is at least 9).

(B) Bonding Agent

The bonding agent comprises a polymerizable monomer and a polymerization initiator, to further enhance the curing of the antibacterial primer and also the adhesive primer noted above (these primers are applied to a tooth prior to the bonding agent), thereby increasing the bonding strength of the adhesive composition of the invention to a tooth. More preferably, the bonding agent contains an acid group-containing polymerizable monomer such as that mentioned above (in an amount of from 1% by weight to 30% by weight) and/or a filler (in an amount of from 1% by weight to 30% by weight). The polymerization initiator in the bonding agent is preferably a photopolymerization initiator.

In the adhesive composition of the invention, in which the adhesive composition is divided into two parts of an adhesive primer and a bonding agent, the photopolymerization initiator in the bonding agent is preferably a combination of an acylphosphine oxide compound and an α-diketone compound.

In the preferred embodiment, the adhesive primer and the bonding agent can be firmly cured within a short period of time to give a cured product having increased bonding strength, especially increased bonding durability.

The acylphosphine oxide compounds include, for example, 2,4,6-trimethylbenzoyldiphenylphosphine oxide, 2,6-diethylbenzoyldiphenylphosphine oxide, 2,6-dimethoxybenzoyldiphenylphosphine oxide, 2,6-dichlorobenzoyldiphenylphosphine oxide, 2,3,5,6-tetramethylbenzoyldiphenylphosphine oxide, benzoyldi-(2,6-dimethylphenyl) phospbonate, 2,4,6-trimethylbenzoylethoxyphenylphosphine oxide, as well as water-soluble acylphosphine oxides such as those disclosed in JP-B-3-57916.

The α-diketone compounds include, for example, camphorquinone, benzil, and 2,3-pentanedione.

The amount of the acylphosphine oxide compound in the bonding agent may generally fall between 0.5% by weight and 10% by weight, preferably between 1% by weight and 7% by weight, more preferably between 2% by weight and 5% by weight, based on the total weight of the bonding agent. The amount of the α-diketone compound to be in the bonding agent may generally fall between 0.01% by weight and 5% by weight, preferably between 0.05% by weight and 3% by weight, more preferably between 0.1% by weight and 1.5% by weight, based on the total weight of the bonding agent.

In general, the acylphosphine oxide compounds and the α-diketone compounds are combined with a reducing agent of, for example, amines, aldehydes, mercaptans or salts of sulfinic acids, as their ability to promote photopolymerization reaction is enhanced. For specific or preferred examples of the reducing agent, referred to are those mentioned hereinabove. The amount of the reducing agent to be in the bonding agent may generally fall between 0.5% by weight and 10% by weight, preferably between 0.1% by weight and 5% by weight, based on the total weight of the bonding agent.

When the bonding agent of the invention will be exposed to the ambient light, the bonding agent is preferably protected from being thickened, gelled or cured owing to the ambient light within a short period of time. For this purpose, it is desirable that the total amount of the acylphosphine oxide compound and the α-diketone compound in the bonding agent is limited to fall between 1% by weight and 6% by weight. More preferably, the ratio of the acylphosphine oxide compound to the α-diketone compound in the bonding agent is so defined that the latter is from 0.01 parts by weight to 0.5 parts by weight based on one part by weight of the former. In the defined ratio, the bonding agent is stable even in the ambient light and its photocurability is high.

If desired, the bonding agent may further contain any other photopolymerization initiators and/or chemical polymerization initiators, in addition to the acylphosphine oxide compound and the α-diketone compound. For examples of the chemical the photopolymerization initiators and polymerization initiators, referred to are those mentioned hereinabove.

(C) Resin Cement

The resin cement comprises a polymerizable monomer, a polymerization initiator and a filler, and this is for further enhancing the curing of the antibacterial primer and also the adhesive primer thereby to increase the bonding strength of the adhesive composition of the invention to a tooth and also to increase the abrasion resistance of the resin cement itself. More preferably, the resin cement contains an acid group-containing polymerizable monomer such as that mentioned above (in an amount of from 1% by weight to 20% by weight), as the monomer is effective for much more enhancing the bonding strength of the composition of the invention. The amount of the filler to be in the resin cement is preferably from 40%, by weight to 80% by weight. As the filler, preferred is an X-ray opaque material, such as barium glass.

The adhesive composition of the invention is used in such a manner that the antibacterial primer in the compositions is first applied to the surface of a tooth, then the adhesive composition is applied on it, and the two are cured thereon. Specific examples of using the adhesive composition are described below, which, however, are not limitative.

(1) Direct Restoration and Repairing with Composite Resin

The antibacterial primer of the invention is applied to the cavity formed in a tooth. Then, this is left as such or forcedly dried with a dental air syringe to remove the volatile solvent. Next, the adhesive composition of the intention is applied on this, and left as such for a while, or it desired, the coated area is blown with a dental air syringe. In that condition, the ingredients in the coated area are cured. Where the adhesive composition is composed of two divided parts of an adhesive primer and a bonding agent, the adhesive primer is first applied to the intended area, then left as such for a predetermined period of time, and thereafter subjected to air blowing. Next, the bonding agent is applied to that area, and the ingredients are cured. The curing may be effected in any desired manner of photopolymerization, a chemical polymerization or dual curing of photopolymerization and chemical polymerization (hereinafter photo/chemical polymerization). Preferred is photopolymerization for which is used an irradiator, or dual curing polymerization, as being easy to perform.

After the adhesive composition has been cured, composite resin or composition for dental restoration is added to the cured area and then cured. By this treatment, the restoration of the tooth is completed.

(2) Indirect Restoration and Repairing with Prosthetic Material

The antibacterial primer of the invention, is first applied to the cavity formed in a tooth. Then, this is left as such or forcedly dried with a dental air syringe to remove the volatile solvent.

Next, the adhesive composition of the invention is applied to a prosthetic material such as a metal alloy, a ceramic, a cured composite resin or the like, which is then pressed against the surface of the tooth having been previously the treated with the antibacterial primer, and then cured. Through the treatment, the restoration of the tooth is completed. In this case, the adhesive composition may be applied to the antibacterial primer-coated surface of the tooth.

Where the adhesive composition is composed of two divided parts of an adhesive primer and a resin cement, the adhesive primer is first applied to the surface of the tooth having been previously treated with the antibacterial primer, then left as such for a predetermined period of time, and thereafter subjected to air blowing. Next the prosthetic material is applied to the treated surface of the sooth along with the resin cement, and cured and bonded to the tooth, The curing may be effected in any desired manner of photopolymerization, chemical polymerization or dual curing of photo/chemical polymerization. In this case, however, the light, from the irradiator for photopolymerization will be often blocked by the prosthetic material. Therefore, for curing the adhesive composition (end also the resin cement) in this case, preferred is chemical polymerization or dual curing polymerization.

In addition, the bonding compositions for dental use of the invention may also be combined with any other bonding ingredients of glass ionomer cement, zinc phosphate cement, polycarboxylate cement, silicate cement, zinc oxide eugenol cement; and also with heat-curable resin, self-curable resin, root canal filler, or temporary sealant.

In particular, for repairing the restorative material having been broken in the mouth, the adhesive compositions of the invention may be applied not only to the tooth restored with the material but also to the repairing material of metals, ceramics or cured composite resins. Further, in their use, the bonding compositions of the invention may be combined with any commercially-available acid etchants or tooth surface cleaners such as hypochlorites, etc.

EXAMPLES

The invention is described in more detail with reference to the following Examples, which, however are not intended to restrict the scope of the invention. The meanings of the abbreviations used hereinabove and also in the following Examples are mentioned below.

| Abbreviations: | Antibacterial Polymerizable Monomers: |
|---|---|
| MDPB: | methacryloyloxydodecylpyridinium bromide |
| MHPC: | methacryloyloxyhexedecylpyrodinium chloride |
| HMPC: | 4-hexadecylmethacryloyloxyethylpyridinium chloride |
| MHBP: | methacryloyloxyethylhexadecylbipyridinium dichloride |
| DMPC: | methacryloyloxyoctadecyltrimethylphosphonium chloride |
| OEPA: | methacryloyloxyoctadecyltriethylphosphonium acetate |
| MEDP: | 4-methacryloyloxyethyldodecylpyridinium chloride |
| VHMS: | di(4-vinylbenzyl)hexadecylmethylammonium methylsulfate |
| DDMC: | di(methacryloyloxyethyl)dodecylmethylammonium chloride |
| BMPS: | methacryloyloxyethyl(4-N-hexadecylpyridinylmethyl) succinate bromide |
| Photopolymerization Initiators: | |
| TMDPO: | 2,4,6-trimethylbenzoyldiphenylphosphine oxide |
| DCOPO: | 2,6-dichlorobenzoyldiphenylphosphine oxide |
| DEOPO: | 2,6-diethylbenzoyidiphenylphosphine oxide |
| CQ: | camphorquinone |
| Reducing Agents, Oxidizing Agents: | |
| BSS: | sodium benzenesulfinate |
| TPBSS: | sodium 2,4,6-1-propylbenzenesulfinate |
| DMAB: | 4-dimethylaminobenzophenone |
| DEPT: | N,N-di(2-hydroxyethyl)-p-toluidine |
| EDMABA: | ethyl 4-dimethylaminobenzoate |
| BPO: | benzoyl peroxide |
| Acid Group-Containing Polymerizable Monomers: | |
| MDP: | 10-methacryloyloxydecyl dihydrogenphosphate |
| MUP: | 11-methacryloyloxyundecyl dihydrogenphosphate |
| Polymerizable Polymers: | |
| Bis-GMA: | bisphenol A diglycidyl dimethacrylate |
| HEMA: | 2-hydroxyethyl methacrylate |
| HD: | 1,6-hexanediol dimethacrylate |

-continued

| Abbreviations: | Antibacterial Polymerizable Monomers: |
|---|---|
| DD: | 1,10-dodecanediol dimethacrylate |
| UDMA: | [2,2,4-trimethylhexamethylenebis(2-carbamoyloxyethyl)] dimethacrylate |
| TH: | N,N'-(2,2,4-trimethylhexamethylene) bis[2-(aminocarboxy)propane-1,3-diol] tetramethacrylate |
| Polymerization Inhibitor: | |
| BHT: | t-butylhydroxytoluene |

Example 1

Ethanol, distilled water and MDPB were mixed in a ratio by weight as indicated in Table 1 to prepare an antibacterial primer. MDP, distilled water, HEMA, HD, CQ and DMAB were mixed in a ratio by weight as indicated in Table 1 to prepare an adhesive composition.

The antibacterial primer and the adhesive composition were tested for the bonding strength, according to the bonding strength test method mentioned below. The data obtained are shown in Table 1. In addition, these were tested for the antibacterial properties according to the antibacterial test methods mentioned below. The data obtained are shown in Table 1.

Bonding Strength Test Method

A bovine anterior tooth was polished in wet with #1000 Silicon Carbide Abrasive Paper (from Nippon Abrasive Paper) to make its surface smooth, then its enamel or dentin was exposed out, and water existing on its surface was blown off with a dental air syringe. An adhesive tape (thickness: about 150 microns) with a hole having a diameter of 3 mm was stuck on the surface of the exposed enamel or dentin. The antibacterial primer of the invention to be tested was first applied to the holed area with a brush, and the volatile solvent was dried up with a dental air syringe. Next, the adhesive composition of the invention to be tested was applied over it also with a brush, then left as such for 60 seconds, and thereafter blown with a dental air syringe to form a film having a thickness of about 100 microns. Then, this was exposed to light for 30 seconds and cured, for which used was a dental light emitter, Litel II (from Gunma Ushio Electric). Next, a commercially-available, photopolymerizable dental composite resin, Clearfill AP-X (from Kuraray) was put on it, covered with a film of Eval® (from Kuraray, film of ethylene/vinyl alcohol copolymer), and pressed against a glass slide superposed thereon. In that condition, this was exposed to light for 40 seconds and cured, for which was used the same light emitter as above. A stainless steel rod having a diameter of 7 mm was attached to the cured surface with a commercially-available dental resin cement, Panavia 21 (from Kuraray) being disposed therebetween, and left as such for 30 minutes. Eight test discs were prepared in all in that manner, and these were all immersed in water at 37° C. After having been thus immersed therein for 24 hours, these were taken out and tested for the bonding strength, for which was used a universal tester (from Instron). At a cross head speed of 2 mm/min, the tensile bonding strength of each test disc was measured. The data of all test discs were averaged.

Antibacterial Test Method 1 (for Evaluating the Antibacterial Properties of Non-cured Discs)

A bovine anterior tooth was smoothly polished in wet with #1000 Silicon Carbide Abrasive Paper (from Nippon Abrasive Paper) to make its dentin exposed out, and cut into disks of 1 mm thick with a diamond saw. An aqueous solution of 40% phosphoric acid was applied to both surfaces of each disc, and left as such for 60 seconds. Then, all discs were washed with running water and thereafter kept in water while they were not used. The dentin surface of each disc was exposed out, and water existing thereon was blown off with a dental air syringe. On the other hand, cells of Streptococcus mutans. IFO13955 which had been pre-incubated for 24 hours in a liquid brain heart infusion (BHI) medium (from Nippon Pharmaceutical) were diluted with a germ-free physiological saline solution to prepare a cell dilution having a cell concentration of $1 \times 10^6$ (CFU/ml), and 100 µl of this cell dilution was inoculated on a BHI-agar medium and uniformly spread thereover with a Conradi rod.

An adhesive tape with a hole having a diameter of 5 mm was stuck on the surface of the dentin disc prepared previously, and the dentin disc with the tape was put on the center of the agar medium prepared as above, and airtightly adhered thereto by gently pressing it. The antibacterial primer of the invention to be tested was applied to the holed area of the tooth disc with a brush, and then the volatile solvent was immediately vaporized away with a dental air syringe. Next, the adhesive composition of the invention to be tested was applied thereto also with a brush, and left as such for 60 seconds. In that condition, the antibacterial primer and the adhesive composition penetrated into the tissue of the dentin disc. The dentin disc was then taken out of it, and the BHI-agar medium was incubated at 37° C. for 48 hours. The growing condition of the cells in the medium was observed, and the antibacterial properties of the tested samples were evaluated according to the following criteria:

++) The cells grew even in the area where the test disc was put, like in the other area.

+) The cell growth was inhibited in the area where the test disc was put, as compared with that in the other area.

−) No cell growth was found in the area where the test disc was put.

Antibacterial Test Method 2 (for Evaluating the Antibacterial Properties of Cured Discs)

An adhesive tape with a hole having an inner diameter of 9 mm was stuck on a film of Eval® (from Kuraray), and the film was fixed horizontally with a metal doughnut (inner diameter: 15 mm, outer diameter: 40 mm, thickness: 0.5 mm) being put thereon. 10 µl of the antibacterial primer of the invention to be tested was dripped into the hole of the metal doughnut, and the volatile solvent was immediately blown off with a dental air syringe. Next, 10 µl of the adhesive composition of the invention to tee tested was dripped thereinto, and cured through exposure to light for 30 seconds with a dental light emitter, Litel II. Next. a commercially-available, photopolymerizable dental composite resin, Clearfill AP-X (from Kuraray) was put on it, covered with a film of Eval® (from Kuraray), and pressed against a glass slide superposed thereon. In that condition, this was exposed to light for 40 seconds and cured, for which was used the same light emitter as above. The cured disc was released from the metal doughnut, and ultrasonically washed with water for 1 hour.

Cells of *Streptococcus mutans*, IF013955 which had been pre-incubated for 24 hours in a liquid brain heart infusion (BHI) medium (from Nippon Pharmaceutical) were diluted with a germ-free physiological saline solution to prepare a cell dilution having a cell concentration of $1\times10^6$ (CFU/ml), and 100 µl of this cell dilution was inoculated on the cured disc. After having left as such for 15 minutes, the cured disc was put on a BHI-agar medium with its cell dilution-coated surface facing the medium, and the cells were recovered from it. Further, the cured disc was put on the other site of the agar medium and pressed against it, and all remaining cells were recovered from it. Thus was prepared a recovered cell sample. On the other hand, 100 µl of the sell dilution prepared previously was directly inoculated on a BHI-agar medium to prepare a control cell sample. Both samples were incubated at 37° C. first anaerobically for 24 hours and then aerobically for 24 hours, and the number of colonies formed in each sample was counted. The cell death percentage on the cured disc was calculated according to the following equation:

Cell Death Percentage $$100 = \frac{\text{number of colonies (in control)} - \text{number of colonies (in recovered sample)}}{\text{number of colonies (in control)}} \times$$

Examples 2 to 7

As in Table 1, various antibacterial primers were prepared in the same manner as in Example 1, except that MDPB was not used but any of HMPC, MHBP, OEPA, VHMS, DDMC or BMPS was used in place of MDPB. The same adhesive composition as in Example 1 was prepared. These antibacterial primers and the adhesive composition were tested for the bonding strength, according to the same bonding strength test method as in Example 1. The data obtained are shown in Table 1. In addition, these were tested for the antibacterial properties also according to the came antibacterial test methods as in Example 1. The data obtained are shown in Table 1.

TABLE 1

| Antibacterial Bonding Composition | Formulation (wt. pts) | | | | | | |
|---|---|---|---|---|---|---|---|
| | Example 1 | Example 2 | Example 3 | Example 4 | Example 5 | Example 6 | Example 7 |
| Antibacterial Primer | | | | | | | |
| Ethanol | 80 | 80 | 80 | 80 | 80 | 80 | 80 |
| Distilled Water | 20 | 20 | 20 | 20 | 20 | 20 | 20 |
| MDPB | 1 | – | – | – | – | – | – |
| HMPC | – | 1 | – | – | – | – | – |
| MHBP | – | – | 1 | – | – | – | – |
| OEPA | – | – | – | 1 | – | – | – |
| VHMS | – | – | – | – | 1 | – | – |
| DDMC | – | – | – | – | – | 1 | – |
| BMPS | – | – | – | – | – | – | 1 |
| Adhesive Composition | | | | | | | |
| MDP | 50 | 50 | 50 | 50 | 50 | 50 | 50 |
| Distilled Water | 1 | 1 | 1 | 1 | 1 | 1 | 1 |
| HEMA | 40 | 40 | 40 | 40 | 40 | 40 | 40 |
| HD | 10 | 10 | 10 | 10 | 10 | 10 | 10 |
| CQ | 2 | 2 | 2 | 2 | 2 | 2 | 2 |
| DMAB | 2 | 2 | 2 | 2 | 2 | 2 | 2 |
| Tensile Bonding Strength: after 24 hours at 37° C. (unit: MPa) | | | | | | | |
| Enamel | 15.6 | 15.1 | 15.3 | 15.5 | 15.5 | 15.6 | 15.2 |
| Dentin | 13.2 | 13.4 | 13.3 | 13.7 | 13.1 | 13.3 | 13.2 |
| Antibacterial Test 1 (cell growth below non-cured disc) | – | – | – | – | – | – | – |
| Antibacterial Test 2 (cell death percentage (%) on cured disc) | 100 | 100 | 100 | 100 | 100 | 100 | 100 |

Comparative Example 1

As in Table 2, a antibacterial primer was prepared in the same manner as in Example 1, except that MDPB was not used herein. The same adhesive composition as in Example 1 was prepared.

The antibacterial primer and the adhesive composition were tested for the bonding strength, according to the same bonding strength test method as in Example 1. The data obtained are shown in Table 2. In addition, these were tested for the antibacterial properties also according to the same antibacterial test methods as in Example 1. The data obtained are shown in Table 2.

Comparative Example 2

As in Table 2, the same adhesive composition as in Example 1 was prepared. The adhesive composition was used singly herein and tested for the bonding strength, according to the same bonding strength test method as in Example 1. The data obtained are shown in Table 2. In addition, this was used singly and tested for the antibacterial properties also according to the same antibacterial test methods as in Example 1. The data obtained are shown in Table 2.

Comparative Examples 3 to 9

As in Table 2, various adhesive compositions were prepared by adding an antibacterial polymerizable monomer of MDPB, HMPC, MHBP, OEPA, VHMS, DDMC OR BMPS was added to the adhesive composition of Example 1. Theme adhesive compositions were tested for the bonding strength, according to the same bonding strength test method as in Example 1. The data obtained are shown in Table 2. In addition, these were tested for the antibacterial properties also according to the same antibacterial test methods as in Example 1. The data obtained are shown in Table 2.

around the discs, though the bonding strength of the compositions was high, like that of the compositions of Examples 1 to 7.

Example 8

MDPB, ethanol, distilled water, TMDPO and BSS were mixed in a ratio by weight as indicated in Table 3 to prepare an antibacterial primer, MDP. HEMA, distilled water and TMDPO were mixed in a ratio by weight as indicated in Table 3 to prepare an adhesive primer. In addition, a bonding agent was prepared from UDMA, HEMA, MDP, TMDPO, CQ, DMAB and a silane-processed quartz powder. These

TABLE 2

| Antibacterial Bonding Composition | Formulation (wt. pts) | | | | | | | | |
|---|---|---|---|---|---|---|---|---|---|
| | Comp. Ex. 1 | Comp. Ex. 2 | Comp. Ex. 3 | Comp. Ex. 4 | Comp. Ex. 5 | Comp. Ex. 6 | Comp. Ex. 7 | Comp. Ex. 8 | Comp. Ex. 9 |
| Antibacterial Primer | | | | | | | | | |
| Ethanol | 80 | | | | | | | | |
| Distilled Water | 20 | — | — | — | — | — | — | — | — |
| Adhesive Composition | | | | | | | | | |
| MDP | 50 | 50 | 50 | 50 | 50 | 50 | 50 | 50 | 50 |
| Distilled Water | 1 | 1 | 1 | 1 | 1 | 1 | 1 | 1 | 1 |
| HEMA | 40 | 40 | 40 | 40 | 40 | 40 | 40 | 40 | 40 |
| HD | 10 | 10 | 10 | 10 | 10 | 10 | 10 | 10 | 10 |
| CQ | 2 | 2 | 2 | 2 | 2 | 2 | 2 | 2 | 2 |
| DMAB | 2 | 2 | 2 | 2 | 2 | 2 | 2 | 2 | 2 |
| MDPB | – | – | 5 | – | – | – | – | – | – |
| HMPC | – | – | – | 5 | – | – | – | – | – |
| MHBP | – | – | – | – | 5 | – | – | – | – |
| OEPA | – | – | – | – | – | 5 | – | – | – |
| VHMS | – | – | – | – | – | – | 5 | – | – |
| DDMC | – | – | – | – | – | – | – | 5 | – |
| BMPS | – | – | – | – | – | – | – | – | 5 |
| Tensile Bonding Strength: after 24 hours at 37° C. (unit: MPa) | | | | | | | | | |
| Enamel | 15.5 | 15.4 | 15.1 | 15.7 | 15.2 | 15.0 | 15.5 | 15.7 | 15.3 |
| Dentin | 13.1 | 13.2 | 13.0 | 12.7 | 13.1 | 13.3 | 13.2 | 13.4 | 13.1 |
| Antibacterial Test 1 (cell growth below non-cured disc) | ++ | ++ | + | + | + | + | + | + | + |
| Antibacterial Test 2 (cell death percentage (%) on cured disc) | 0 | 0 | 58 | 60 | 59 | 66 | 68 | 61 | 64 |

As in Table 1, the bonding compositions of Examples 1 to 7 (these are composed of an antibacterial primer comprising an antibacterial polymerizable monomer and a volatile solvent, and an adhesive composition) all had a high bonding strength of about 15 MPa to the tooth enamel and about 13 MPa to the tooth dentin. In addition, these completely killed the cells below their non-cured discs in the antibacterial test 1. The data in the test 1 support the strong antibacterial properties of the non-cured bonding compositions. In the antibacterial test 2, the cells adhered on the cured discs of these bonding compositions were also completely killed. The data in the test 2 support the strong antibacterial properties of the cured bonding compositions.

However, as in Table 2, the non-cured and cured discs of the compositions of Comparative Examples 1 and 2 (these do not contain an antibacterial polymerizable monomer) had no antibacterial properties, though their bonding strength was good.

On the other hand. the antibacterial properties of the non-cured and cured discs of the compositions of Comparative Examples 3 to 9 (these contain an antibacterial polymerizable monomer) were not enough to kill the cells were tested for the tensile bonding strength to tooth, according to the bonding strength test method mentioned below. The data obtained are shown in Table 3. In addition, these were tested for the antibacterial properties according to the antibacterial test methods mentioned below. The data obtained are shown in Table 3.

Bonding Strength Test Method

In the same manner as in the test method for Example 1 mentioned above, a bovine anterior tooth was polished to make its enamel or dentin exposed out, and water existing on its surface was blown off with a dental air syringe. An adhesive tape (thickness: about 150 microns) with a hole having a diameter of 3 mm was stuck on the surface of the exposed enamel or dentin. The antibacterial primer of the invention to be tested was first applied to the holed area with a brush, and the volatile solvent was dried up with a dental air syringe. Next, the adhesive primer of the invention to be tested was applied over it also with a brush, and then left as such for 30 seconds, and its excessive part was blown off with a dental air syringe. Next, the bonding agent to be tested was further applied thereover also with a brush, and again blown with a dental air syringe to form a film having a thickness of about 100 microns. Then, this was exposed to light for 10 seconds and cured, for which used was a dental light emitter, Litel II. Next, like in Example 1, a photopolymerizable dental composite resin, Clearfill AP-X (from Kuraray} was put on it, and cured thereon. Then, this was put in water at 37° C. Eight test discs were prepared in all in that manner, and these were all immersed in water at 37° C. After having been thus immersed therein for 24 hours, these were taken out and tested for the tensile bonding strength. The data of all test discs were averaged.

Antibacterial Test Method 1 (for Evaluating the Antibacterial Properties of Non-cured Discs)

In the same manner as in Example 1, a bovine dentin disc was prepared. Also in the same manner as in Example 1, cells of *Streptococcus mutans*, IF013955 which had been pre-incubated for 24 hours in a liquid brain heart infusion (BHI) medium (from Nippon Pharmaceutical) were diluted with a germ-free physiological saline solution to prepare a cell dilution having a cell concentration of $1 \times 10^6$ (CFU/ml), and 100 µl of this cell dilution was inoculated on a BHI-agar medium and uniformly spread thereover with a Conradi rod.

An adhesive tape with a hole having a diameter of 5 mm was stuck on the surface of the dentin disc prepared previously, and the dentin disc with the tape was put on the center of the agar medium prepared as above, and airtightly adhered thereto by gently pressing it. The antibacterial primer of the invention to be tested was applied to the holed area of the dentin disc with a brush, and then the volatile solvent was immediately vaporized away with a dental air syringe. Next, the adhesive primer to be tested was applied thereto also with a brush, and left as such for 30 seconds. After this, the bonding agent to be tested was applied thereover, and left as such for 30 seconds. In that condition, the antibacterial primer, the adhesive primer and the bonding agent penetrated into the tissue of the dentin disc. The dentin disc was then taken out of it, and the BHI-agar medium was incubated at 37° C. for 48 hours. The growing condition of the cells in the medium was observed, and the antibacterial properties of the tested samples were evaluated according to the same criteria as in Example 1.

Antibacterial Test Method 2 (for Evaluating the Antibacterial Properties of Cured Discs)

In the same manner as in Example 1, an adhesive tape with a hole having an inner diameter of 9 mm was stuck on a film of Eval®, and the film was fixed horizontally with a metal doughnut being put thereon. 10 µl of the antibacterial primer of the invention to be tested was dripped into the hole of the metal doughnut, and the volatile solvent was immediately blown off with a dental air syringe. Next, 10 µl of the adhesive primer of the invention to be tested was dripped thereinto, and blown with a dental air syringe. Then, the bonding agent of the invention to be tested was applied over this with a brush to form a film having a thickness of about 100 µm. This was exposed to light for 10 seconds and cured, for which was used a dental light emitter, Litel II. Next, a commercially-available, photopolymerizable dental composite resin, Clearfill AP-X was put on it, covered with a film of Eval, and pressed against a glass slide superposed thereon. In that condition, this was exposed to light for 40 seconds and cured, for which was used the same light emitter as above. The cured disc was released from the metal doughnut, and ultrasonically washed with water for 1 hour. The cell death percentage on the discs prepared herein was obtained in the same manner as in Example 1.

Example 9

DMPC, ethanol, distilled water, TMDPO and BSS were mixed in a ratio by weight as indicated in Table 3 to prepare an antibacterial primer. On the other hand, the same adhesive primer and bonding agent as in Example 8 were prepared. These were tested for the bonding strength, according to the same bonding strength test method as in Example 8. The data obtained are shown in Table 3. In addition, these were tested for the antibacterial properties also according to the same antibacterial test methods as In Example 8. The data obtained are shown in Table 3.

Comparative Example 10

The same adhesive primer and bonding agent as in Example 8 were prepared. These were tested for the bonding strength, according to the same bonding strength test method as in Example 8. The date obtained are shown in Table 3. In addition, these were tested for the antibacterial properties also according to the same antibacterial test methods as in Example 8. The data obtained are shown in Table 3.

Comparative Examples 11 and 12

As in Table 3, adhesive primers were prepared by adding any of MDPB or DMPC to the adhesive primer of Example 8. On the other hand, the same bonding agent as in Example 8 was prepared. Each adhesive primer was combined the bonding agent and tested for the bonding strength, according to the same bonding strength test method as in Example 8. The data obtained are shown in Table 3. In addition, these were tested for the antibacterial properties also according to the same antibacterial test methods as in Example 8. The data obtained are shown in Table 3.

TABLE 3

| | Formulation (wt. pts) | | | | |
|---|---|---|---|---|---|
| Antibacterial Bonding Composition | Example 8 | Example 9 | Comp. Ex. 10 | Comp. Ex. 11 | Comp. Ex. 12 |
| Antibacterial Primer | | | | | |
| MDPB | 1 | – | | | |
| DMPC | – | 1 | | | |
| Ethanol | 70 | 70 | | | |
| Distilled Water | 30 | 30 | — | — | — |
| TMDPO | 0.2 | 0.2 | | | |
| BSS | 1 | 1 | | | |
| Adhesive Composition | | | | | |
| Adhesive Primer | | | | | |
| MDP | 10 | 10 | 10 | 10 | 10 |
| HEMA | 40 | 40 | 40 | 40 | 40 |
| Distilled Water | 50 | 50 | 50 | 50 | 50 |
| TMDPO | 1 | 1 | 1 | 1 | 1 |
| MDPB | – | – | – | 5 | – |
| DMPC | – | – | – | – | 5 |
| Bonding Agent | | | | | |
| UDMA | 60 | 60 | 60 | 60 | 60 |
| HEMA | 35 | 35 | 35 | 35 | 35 |
| MOP | 5 | 5 | 5 | 5 | 5 |
| TMDPO | 2 | 2 | 2 | 2 | 2 |
| CQ | 0.5 | 0.5 | 0.5 | 0.5 | 0.5 |
| DMAB | 0.5 | 0.5 | 0.5 | 0.5 | 0.5 |
| Silane-processed Quartz Powder | 10 | 10 | 10 | 10 | 10 |
| Tensile Bonding Strength: after 24 hours at 37° C. (unit: MPa) | | | | | |
| Enamel | 20.1 | 20.5 | 19.1 | 20.0 | 20.2 |
| Dentin | 19.3 | 19.5 | 19.2 | 18.9 | 19.1 |
| Antibacterial Test 1 (cell growth below non-cured disc) | – | – | ++ | + | + |

TABLE 3-continued

| Antibacterial Bonding Composition | Formulation (wt. pts) | | | | |
|---|---|---|---|---|---|
| | Example 8 | Example 9 | Comp. Ex. 10 | Comp. Ex. 11 | Comp. Ex. 12 |
| Antibacterial Test 2 (cell death percentage (%) on cured disc) | 100 | 100 | 0 | 68 | 66 |

As in Table 3, the bonding compositions of Examples 8 and 9 (these are composed of an antibacterial primer comprising an antibacterial polymerizable monomer and a volatile solvent, and an adhesive composition) all had a high bonding strength of about 20 MPa to the tooth enamel and about 19 MPa to the tooth dentin. In addition, these completely killed the cells below their non-cured discs in the antibacterial test 1. The data in the test 1 support the strong antibacterial properties of the non-cured bonding compositions. In the antibacterial test 2, the cells adhered on the cured discs of these bonding compositions were also completely killed. The data in the test 2 support the strong antibacterial properties of the cured bonding compositions.

However, the non-cured and cured discs of the composition of Comparative Example 10 (this does not contain an antibacterial polymerizable monomer) had no antibacterial properties, though their bonding strength was good. On the other hand, the antibacterial properties of the non-cured and cured discs of the compositions of Comparative Examples 11 and 12 (in these, the adhesive primer contains an antibacterial polymerizable monomer) were not enough to kill the cells around the discs, though the bonding strength of the compositions was high, like that of the antibacterial bonding compositions of Examples 8 and 9.

Example 10

MDPB and ethanol were mixed in a ratio by weight an indicated in Table 4 to prepare an antibacterial primer. MDP, HEMA, distilled water, DEPT and CQ were mixed in a ratio by weight as indicated in Table 4 to prepare an adhesive primer. In addition, a bonding agent was prepared from Bis-GMA, HEMA, TMDPO, CQ and DMAB by mixing them in a ratio by weight as indicated in Table 4. These were tested for the tensile bonding strength to tooth and for the antibacterial properties, according to the same bonding strength test method and the same antibacterial test methods as in Example 8. The data obtained are shown in Table 4.

Example 11

MDPB and ethanol were mixed in a ratio by weight as indicated in Table 4 to prepare an antibacterial primer. MDP, HEMA, DEPT and CQ were mixed in a ratio by weight as indicated in Table 4 to prepare an adhesive primer. In addition, the same bonding agent an in Example 10 was prepared. These were tested for the tensile bonding strength according to the same bonding strength test as in Example 8. The data obtained are shown in Table 4. In addition, these were tested for the antibacterial properties also according to the same antibacterial test methods as in Example 8. The data obtained are shown in Table 4.

Comparative Example 13

The same adhesive primer and bonding agent as in Example 11 were prepared. These were tested for the bonding strength, according to the same bonding strength test method as in Example 8. The date obtained are shown in Table 4. In addition, these were tested for the antibacterial properties also according to the same antibacterial test methods as in Example 8. The data obtained are shown in Table 4.

Comparative Examples 14 and 15

As in Table 4, adhesive primers were prepared by adding MDPB to any of the adhesive primers of Examples 10 and 11. On the other hand, the same bonding agent as in Example 10 was prepared. Each adhesive primer was combined the bonding agent and tested for the bonding strength, according to the same bonding strength test method as in Example 8. The data obtained are shown in Table 4. In addition, these were tested for the antibacterial properties also according to the same antibacterial test methods as in Example 8. The data obtained are shown in Table 4.

TABLE 4

| Antibacterial Bonding Composition | Formulation (wt. pts) | | | | |
|---|---|---|---|---|---|
| | Example 10 | Example 11 | Comp. Ex. 13 | Comp. Ex. 14 | Comp. Ex. 15 |
| Anti-bacterial Primer | | | | | |
| MDPB | 5 | 5 | | | |
| Ethanol | 100 | 100 | — | — | — |
| Adhesive Composition | | | | | |
| Adhesive Primer | | | | | |
| MDP | 15 | 15 | 15 | 15 | 15 |
| HEMA | 60 | 80 | 80 | 60 | 80 |
| Distilled Water | 25 | – | – | 25 | – |
| MDPB | – | – | – | 5 | 5 |
| DEPT | 3 | 3 | 3 | 3 | 3 |
| CQ | 1 | 1 | 1 | 1 | 1 |
| Bonding Agent | | | | | |
| Bis-GMA | 65 | 65 | 65 | 65 | 65 |
| HEMA | 35 | 35 | 35 | 35 | 35 |
| TMDPO | 3 | 3 | 3 | 3 | 3 |
| CQ | 1 | 1 | 1 | 1 | 1 |
| DMAB | 1 | 1 | 1 | 1 | 1 |
| Tensile Bonding Strength: after 24 hours at 37° C. (unit: MPa) | | | | | |
| Enamel | 20.7 | 16.8 | 16.6 | 20.1 | 16.5 |
| Dentin | 19.9 | 16.6 | 16.1 | 19.2 | 16.4 |
| Antibacterial Test 1 (cell growth below non-cured disc) | – | – | ++ | + | + |
| Antibacterial Test 2 (cell death percentage (%) on cured disc) | 100 | 100 | 0 | 65 | 64 |

As in Table 4, the bonding compositions of Examples 10 and 11 (these are composed of an antibacterial primer comprising an antibacterial polymerizable monomer and a volatile solvent, an adhesive primer, and a bonding agent) all had a high bonding strength of about 16 to 20 MPa to the tooth enamel and also to the tooth dentin. In addition, these completely killed the cells below their non-cured discs in the antibacterial test 1. The data in the test 1 support the strong antibacterial properties of the non-cured bonding compositions. In the antibacterial test 2, the cells adhered on the cured discs of these bonding compositions were also completely killed. The data in the test 2 support the strong antibacterial properties of the cured bonding compositions.

However, the non-cured and cured discs of the composition of Comparative Example 13 (this does not contain an antibacterial polymerizable monomer) had no antibacterial properties, though their bonding strength was good. On the other hand, the antibacterial properties of the non-cured and cured discs of the compositions of Comparative Examples 14 and 15 (in these, the adhesive primer contains an antibacterial polymerizable monomer) were not enough to kill the cells around the discs, though the bonding strength of the compositions was high, like that of the compositions of Examples 10 and 11.

Example 12

MHPC and ethanol were mixed in a ratio by weight as indicated in Table 5 to prepare an antibacterial primer. MDP, HEMA, distilled water, CQ, DMAB and DEPT were mixed in a ratio by weighs as indicated in Table 5 to prepare an adhesive primer. In addition, TH, DD, MDP, TMDPO, BPO and silane-processed quartz powder were mixed in a ratio by weight as indicated in Table 5 to prepare a resin cement (A); and TH, HEMA, DD, DEPT, TPBSS and silane-processed quartz powder were mixed in a ratio by weight as indicated in Table 5 to prepare a resin cement (B). These were tested for the bonding strength to tooth, according to the bonding strength test method mentioned below. In addition, these were tested for the antibacterial properties according to the antibacterial test methods mentioned below.

Bonding Strength Test Method

In the same manner as in the test method for Example 1 mentioned above, a bovine anterior tooth was polished to make its enamel or dentin exposed out, and water existing on its surface was blown off with a dental air syringe. An adhesive tape (thickness: about 150 microns) with a hole having a diameter of 5 mm was stuck on the surface of the exposed enamel or dentin. The antibacterial primer of the invention to be tested was first applied to the holed area with a brush, and the volatile solvent was dried up with a dental air syringe. Next, the adhesive primer of the invention to be tested was applied over it also with a brush, and then left as such for 30 seconds, and its excessive part was blown off with a dental air syringe.

Next, the resin cement (A) and the resin cement (B) of the invention to be tested were mixed in ratio of 1/1 to prepare a paste, and the paste was applied to a stainless steel rod having a diameter of 7 mm. This was pressed against the adhesive primer-coated surface of the tooth having been treated as above. After left as such for 30 minutes, this was immersed in water at 37° C. After having been thus immersed therein for 24 hours, this was taken out and its tensile bonding strength was measured.

Antibacterial Test Method 1 (for Evaluating the Antibacterial Properties of Non-cured Discs)

In the same manner as in Example 1, a bovine dentin disc was prepared. Also in the same manner as in Example 1, cells of *Streptococcus mutans*, IF013955 which had been pre-incubated for 24 hours in a liquid brain heart infusion (BHI) medium (from Nippon Pharmaceutical) were diluted with a germ-free physiological saline solution to prepare a cell dilution having a cell concentration of $1\times10^6$ (CFU/ml), and 100 µl of this cell dilution was inoculated on a BHI-agar medium and uniformly spread thereover with a Conradi rod.

An adhesive tape with a hole having a diameter of 5 mm was stuck on the surface of the dentin disc prepared previously (thickness: 1 mm), and the dentin disc with the tape was put on the center of the BHI-agar medium prepared as above, and airtightly adhered thereto. The antibacterial primer of the invention to be tested was applied to the holed area of the tooth disc with a brush, and then the volatile solvent was immediately vaporized away with a dental air syringe. Next, the adhesive primer to be tested was applied thereto also with a brush, and left as such for 30 seconds. In that condition, the antibacterial primer and the adhesive primer penetrated into the tissue of the dentin disc. The dentin disc was then taken out of it, and the agar medium was incubated at 37° C. for 48 hours. The growing condition of the cells in the medium was observed, and the antibacterial properties of the tested samples were evaluated according to the same criteria as in Example 1.

Antibacterial Test Method 2 (for Evaluating the Antibacterial Properties of Cured Discs)

In the same manner as in Example 1, an adhesive tape with a hole having an inner diameter of 9 mm was stuck on a film of Eval, and the film was fixed horizontally with a metal doughnut being put thereon. 10 µl of the antibacterial primer of the invention to be tested was dripped into the hole of the metal doughnut, and the volatile solvent was immediately blown off with a dental air syringe. Next, 10 µl of the adhesive primer of the invention to be tested was dripped thereinto, and blown with a dental air syringe. Then, a paste of the resin cement (A) and the resin cement (B) of the invention to be tested, as prepared by mixing them in a ratio of 1/1, was applied over this, covered with an Eval film, and pressed against a glass slide superposed thereon. In that condition, this was left as such for 60 minutes and cured. The cured disc was released from the metal doughnut, and ultrasonically washed with water for 1 hour. The cell death percentage on the discs prepared herein was obtained in the same manner as in Example 1.

Example 13

MEDP and ethanol were mixed in a ratio by weight as indicated in Table 5 to prepare an antibacterial primer. On the other hand, the same adhesive primers resin cement (A) and resin cement (B) as in Example 12 were prepared. These were tested for the bonding strength, according to the same bonding strength test method as in Example 12. The data obtained are shown in Table 5. In addition, these were tested for the antibacterial properties also according to the same antibacterial test methods as in Example 12. The data obtained are shown in Table 5.

Comparative Example 16

The same adhesive primer, resin cement (A) and resin cement (B) as in Example 12 were prepared. These were tested for the bonding strength, according to the same bonding strength test method as in Example 12. The data obtained are shown in Table 5. In addition, these were tested for the antibacterial properties also according to the same antibacterial test methods as in Example 12. The data obtained are shown in Table 5.

Comparative Examples 17 and 18

As in Table 5, adhesive primers were prepared by adding any of MHPC or MEDP to the adhesive primer of Example 12. On the other hand, the same resin cement (A) and resin cement (B) as in Example 12 was prepared. There were combined and tested for the bonding strength, according to the same bonding strength test method as in Example 12. The data obtained are shown in Table 5. In addition, these were tested for the antibacterial properties also according to the same antibacterial test methods as in Example 12. The data obtained are shown in Table 5.

TABLE 5

| Antibacterial Bonding Composition | Formulation (wt. pts) | | | | |
|---|---|---|---|---|---|
| | Example 12 | Example 13 | Comp. Ex. 16 | Comp. Ex. 17 | Comp. Ex. 18 |
| Antibacterial Primer | | | | | |
| MHPC | 1 | – | | | |
| MEDP | – | 1 | — | — | — |
| Ethanol | 100 | 100 | | | |
| Adhesive Composition | | | | | |
| Adhesive Primer | | | | | |
| MDP | 10 | 10 | 10 | 10 | 10 |
| HEMA | 40 | 40 | 40 | 40 | 40 |
| Distilled Water | 50 | 50 | 50 | 50 | 50 |
| CQ | 0.5 | 0.5 | 0.5 | 0.5 | 0.5 |
| DMAB | 1 | 1 | 1 | 1 | 1 |
| DEPT | 5 | 5 | 5 | 5 | 5 |
| MHPC | – | – | – | 5 | – |
| MEDP | – | – | – | – | 5 |
| Resin Cement | | | | | |
| A | | | | | |
| TH | 60 | 60 | 60 | 60 | 60 |
| DD | 5 | 5 | 5 | 5 | 5 |
| MDP | 30 | 30 | 30 | 30 | 30 |
| TMDPO | 2 | 2 | 2 | 2 | 2 |
| BPO | 2 | 2 | 2 | 2 | 2 |
| Silane-processed Quartz Powder | 300 | 300 | 300 | 300 | 300 |
| B | | | | | |
| TH | 70 | 70 | 70 | 70 | 70 |
| HEMA | 20 | 20 | 20 | 20 | 20 |
| DD | 10 | 10 | 10 | 10 | 10 |
| DEPT | 1 | 1 | 1 | 1 | 1 |
| TPBSS | 1 | 1 | 1 | 1 | 1 |
| Silane-processed Quartz Powder | 300 | 300 | 300 | 300 | 300 |
| Tensile Bonding Strength: after 24 hours at 37° C. (unit: MPa) | | | | | |
| Enamel | 20.5 | 20.0 | 20.3 | 20.2 | 20.0 |
| Dentin | 13.4 | 13.3 | 13.1 | 12.6 | 12.3 |
| Antibacterial Test 1 (cell growth below non-cured disc) | – | – | ++ | + | + |
| Antibacterial Test 2 (cell death percentage (%) on cured disc) | 100 | 100 | 0 | 61 | 63 |

As in Table 5, the bonding compositions of Examples 12 and 13 (these are composed of an antibacterial primer comprising an antibacterial polymerizable monomer and a volatile solvent, an adhesive primer, a resin cement (A), and a resin cement(B) all had a high bonding strength of about 20 MPa to the tooth enamel and about 13 MPa to the tooth dentin. In addition, these completely killed the cells below their non-cured discs in the antibacterial test 1. The data in the test 1 support the strong antibacterial properties of the non-cured bonding compositions. In the antibacterial test 2, the cells adhered on the cured discs of these bonding compositions were also completely killed. The data in the test 2 support the strong antibacterial properties of the cured bonding compositions.

However, the non-cured and cured discs of the composition of Comparative Example 16 (this does not contain an antibacterial polymerizable monomer) had no antibacterial properties, though their bonding strength was good. On the other hand, the antibacterial properties of the non-cured and cured discs of the compositions of Comparative Examples 17 and 18 (in these, the adhesive primer contains an antibacterial polymerizable monomer) were not enough to kill the cells around the discs, though the bonding strength of the compositions was high, like that of the compositions of Examples 12 and 13.

Example 14

MUP, HEMA and distilled water were mixed in a ratio by weight as indicated in Table 6 to prepare an adhesive primer. On the other hand, UDMA, HEMA, TMDPO, CQ, EDMABA and DEPT were mixed in a ratio by weight as indicated in Table 6 to prepare a bonding agent.

The adhesive primer and the bonding agent were tested according to the photo-curing test methods mentioned below, in which the photo-curing time and the photo-cured depth were measured. The data obtained are shown in Table 6. In addition, these were tested for the bonding strength according to the same bonding strength test as in Example 8. Further, these were subjected to a bonding curability test, in which the bonded discs to be tested were exposed to 10000 heat cycles (one cycle comprises immersing the bonded discs in water at 37° C. for 24 hours, then in cold water at 4° C. and hot water at 60° C. for 1 minute each), and their bonding strength was measured. The data obtained are also in Table 6.

Method for Measuring Photo-curing Time (1)

A bovine anterior sooth was smoothly polished in wet with #1000 Silicon Carbide Abrasive Paper (from Nippon Abrasive Paper) to make its dentin exposed out, and water existing on its surface was blown off with a dental air syringe. The adhesive primer to be tested was applied to the exposed dentin surface with a brush, then left as such for 30 seconds, and thereafter dried with an air syringe. Next, a washer with a hole having a depth of 0.8 mm and a diameter of 4 mm was put on it, and the hole was filled with the bonding agent to be tested. With the tip of a thermocouple being inserted into the hole in that condition, the sample was exposed to light, for which used was a dental light emitter, Litel II (from Gunma Ushio Electric). During the exposure, the temperature change in the sample was recorded through the thermocouple, from which was obtained the time from the start of the exposure to the heat peak. The time indicates the photo-curing time for the sample.

Method for Measuring Photo-cured Depth (2)

A mold having a diameter of 4 mm and a depth of 5 mm was filled with the bonding agent to be tested, and exposed to light for 10 seconds from a dental light emitter, Litel (from Gunma Ushio Electric). Then, the disc sample was released from the mold, and the non-cured bonding agent was wiped away with tissue paper. The cured sample which was still soft was compressed under a load of 500 g, and its thickness was measured with a vernier micrometer.

Examples 15 to 17 and Comparative Examples 19 to 22

The same adhesive primer as in Example 14 and as in Table 6 was prepared. In addition, bonding agents were prepared by mixing UDMA or Bis-GMA, and any of HD, HEMA, TMDPO, DCDPO, CQ, EDMABA and DEPT in a ratio by weigh as indicated in Table 6.

The adhesive primer and the bonding agents were tested for the photo-curing time, the photo-cured depth and the bonding strength, according to the same photo-curing tests and bonding strength tests as in Example 14. The data obtained are shown in Table 6.

TABLE 6

| Adhesive Composition | Formulation (wt. pts) | | | | | | | |
|---|---|---|---|---|---|---|---|---|
| | Ex. 14 | Ex. 15 | Ex. 16 | Ex. 17 | Comp. Ex. 19 | Comp. Ex. 20 | Comp. Ex. 21 | Comp. Ex. 22 |
| Adhesive Primer | | | | | | | | |
| MUP | 20 | 20 | 20 | 20 | 20 | 20 | 20 | 20 |
| HEMA | 40 | 40 | 40 | 40 | 40 | 40 | 40 | 40 |
| Distilled Water | 40 | 40 | 40 | 40 | 40 | 40 | 40 | 40 |
| Bonding Agent | | | | | | | | |
| UDMA | 70 | 70 | – | – | 70 | – | 70 | – |
| Bis-GMA | – | – | 45 | 45 | – | 45 | – | 45 |
| HD | – | – | 20 | 20 | – | 20 | – | 20 |
| HEMA | 30 | 30 | 35 | 35 | 30 | 35 | 30 | 35 |
| TMDPO | 2.5 | – | 2.5 | – | 2.8 | 2.8 | – | – |
| DCDPO | – | 2.5 | – | 2.5 | – | – | – | – |
| CQ | 0.3 | 0.3 | 0.3 | 0.3 | – | – | 2.8 | 2.8 |
| EDMABA | 1 | 1 | 1 | 1 | 1 | 1 | 1 | 1 |
| DEPT | 0.5 | 0.5 | 0.5 | 0.5 | 0.5 | 0.5 | 0.5 | 0.5 |
| Photo-curing Time (sec) | 8.2 | 8.4 | 8.2 | 8.2 | 9.8 | 9.7 | 14.8 | 14.2 |
| Photo-cured Depth (mm) | 2.0 | 2.1 | 2.0 | 1.9 | 0.5 | 0.4 | 1.1 | 1.0 |
| Tensile Bonding Strength (unit: MPa) | | | | | | | | |
| After 24 hours at 37° C. | | | | | | | | |
| Enamel | 20.1 | 20.3 | 20.4 | 20.2 | 19.7 | 19.6 | 18.1 | 19.8 |
| Dentin | 19.0 | 18.8 | 18.7 | 21.3 | 19.3 | 19.1 | 16.2 | 16.8 |
| After Heat Cycle Test | | | | | | | | |
| Enamel | 21.2 | 21.0 | 20.3 | 19.5 | 12.1 | 12.5 | 6.8 | 6.7 |
| Dentin | 17.6 | 17.5 | 17.9 | 18.3 | 11.5 | 11.6 | 5.8 | 5.9 |

As in Table 6, it is understood that the adhesive compositions of Examples 14 to 17 (in these, the bonding agent comprises an acylphosphine oxide compound and CQ both serving as a photopolymerization initiator) cured within a period of 10 seconds, and that their photo-cured depth reached about 2 mm after exposure for 10 seconds. The data support the good photocurability of the compositions. In addition, in the heat cycle test for the bonding durability, the bonding strength of the compositions decreased little after heat cycles. However, the adhesive compositions of Comparative Examples 19 and 20 (in these, the bonding agent comprises TMDPO only as the photopolymerization initiator) had a photo-cured depth of about 0.5 mm even though they cured within 10 seconds. The data indicate that the photocurability of these comparative compositions is not satisfactory. In addition, the bonding strength of the comparative compositions lowered after heat cycles. On the other hand, the adhesive compositions of Comparative Examples 21 and 22 (in these, the bonding agent comprises CQ only as the photopolymerization initiator) could not be completely cured within 10 seconds, and their photo-cured depth was only 1 mm or so. The data indicate that the photocurability of these comparative compositions is not good. In addition the bonding strength of the comparative compositions noticeably lowered after heat cycles.

Examples 18 to 21 and Comparative Examples 23 to 26

MDP, HEMA, CQ, DMAB and distilled water were mixed in a ratio by weight as indicated in Table 7 to prepare adhesive primers. On the other hand, bonding agents were prepared by mixing UDMA or Bis-GMA, and any of HD, HEMA. MDP, TMDPO, DEDPO, CQ, EDMABA and BHT in a ratio by weigh as indicated in Table 7.

The adhesive primer and the bonding agents were tested for the photo-curing time, the photo-cured depth and the bonding strength, according to the same photo-curing tests and bonding strength tests as in Example 14. The data obtained are shown in Table 7.

TABLE 7

| Adhesive Composition | Formulation (wt. pts) | | | | | | | |
|---|---|---|---|---|---|---|---|---|
| | Ex. 18 | Ex. 19 | Ex. 20 | Ex. 21 | Comp. Ex. 23 | Comp. Ex. 24 | Comp. Ex. 25 | Comp. Ex. 26 |
| Adhesive Primer | | | | | | | | |
| MDP | 15 | 15 | 15 | 15 | 15 | 15 | 15 | 15 |
| HEMA | 40 | 40 | 40 | 40 | 40 | 40 | 40 | 40 |
| CQ | 0.3 | 0.3 | 0.3 | 0.3 | 0.3 | 0.3 | 0.3 | 0.3 |
| DMAB | 0.5 | 0.5 | 0.5 | 0.5 | 0.5 | 0.5 | 0.5 | 0.5 |
| Distilled Water | 45 | 45 | 45 | 45 | 45 | 45 | 45 | 45 |

TABLE 7-continued

| Adhesive Composition | Formulation (wt. pts) | | | | | | | |
|---|---|---|---|---|---|---|---|---|
| | Ex. 18 | Ex. 19 | Ex. 20 | Ex. 21 | Comp. Ex. 23 | Comp. Ex. 24 | Comp. Ex. 25 | Comp. Ex. 26 |
| Bonding Agent | | | | | | | | |
| UDMA | 65 | 65 | – | – | 65 | – | 65 | – |
| Bis-GMA | – | – | 40 | 40 | – | 40 | – | 40 |
| HD | – | – | 25 | 25 | – | 25 | – | 25 |
| HEMA | 30 | 30 | 30 | 30 | 30 | 30 | 30 | 30 |
| MDP | 5 | 5 | 5 | 5 | 5 | 5 | 5 | 5 |
| TMDPO | 2.5 | – | 2.5 | – | 2.8 | 2.8 | – | – |
| DEDPO | – | 2.5 | – | 2.5 | – | – | – | – |
| CQ | 0.3 | 0.3 | 0.3 | 0.3 | – | – | 2.8 | 2.8 |
| EDMABA | 1 | 1 | 1 | 1 | 1 | 1 | 1 | 1 |
| BHT | 0.05 | 0.05 | 0.05 | 0.05 | 0.05 | 0.05 | 0.05 | 0.05 |
| Photo-curing Time (sec) | 8.2 | 8.4 | 8.3 | 8.4 | 9.9 | 9.8 | 13.5 | 13.6 |
| Photo-cured Depth (mm) | 2.2 | 2.1 | 2.1 | 2.2 | 0.5 | 0.5 | 1.6 | 1.6 |
| Tensile Bonding Strength (unit: MPa) | | | | | | | | |
| After 24 hours at 37° C. | | | | | | | | |
| Enamel | 22.3 | 22.5 | 22.6 | 22.4 | 21.9 | 21.8 | 19.4 | 18.9 |
| Dentin | 21.2 | 21.9 | 21.8 | 22.1 | 19.8 | 19.7 | 17.5 | 17.4 |
| After Heat Cycle Test | | | | | | | | |
| Enamel | 22.1 | 21.6 | 21.1 | 21.3 | 13.7 | 13.8 | 8.7 | 8.6 |
| Dentin | 20.6 | 20.8 | 19.7 | 20.5 | 13.8 | 13.9 | 8.8 | 8.6 |

As in Table 7, it is understood that the adhesive compositions of Examples 18 to 21 (in these, the bonding agent comprises an acylphosphine oxide compound and CQ both serving as a photopolymerization initiator) cured within a period of 10 seconds, and that their photo-cured depth reached about 2 mm after exposure for 10 seconds. The data support the good photocurability of the compositions. In addition, in the heat cycle test for the bonding durability, the bonding strength of the compositions decreased little after heat cycles. However, the adhesive compositions of Comparative Examples 23 and 24 (in these, the bonding agent comprises TMDPO only as the photopolymerization initiator) had a photo-cured depth of about 0.5 mm even though they cured within 10 seconds. The data indicate that the photocurability of these comparative compositions is not satisfactory. In addition, the bonding strength of the comparative compositions lowered after heat cycles. On the other hand, the adhesive compositions of Comparative Examples 25 and 26 (in these, the bonding agent comprises CQ only as the photopolymerization initiator) could not be completely cured within 10 seconds, and their photo-cured depth was only 1.5 mm or so. The data indicate that the photocurability of these comparative compositions is not good. In addition, the bonding strength of the comparative compositions noticeably lowered after heat cycles.

Examples 22 to 26 and Comparative Examples 27 to 29

The adhesive primer of Example 20 was again prepared herein. On the other hand, different bonding agents were prepared in the same manner as in Example 20 except that the proportions of TDMPO and CQ both serving as a photopolymerization initiator were varied. The adhesive primer and the bonding agents were tested for the bonding strength, according to the same bonding strength tests as in Example 14. The data obtained are shown in Table 8. In addition, the bonding agents were tested for the light stability according to the light stability test mentioned below. The data obtained are shown in Table 8.

Light Stability Test

A sampling dish was put on a laboratory table, and a fluorescent lamp with a movable stand was so fitted thereto that the illuminance at the dish could be 1,000 luxes. 0.03 g of the bonding agent to be tested was put into the dish, and exposed to the fluorescent lamp under that condition. The time before a part of the bonding agent in the dish cured or gelled was measured.

TABLE 8

| | Ex. 22 | Ex. 23 | Ex. 24 | Ex. 25 | Ex. 26 | Comp. Ex. 27 | Comp. Ex. 28 | Comp. Ex. 29 |
|---|---|---|---|---|---|---|---|---|
| TMDPO (wt. pts.) | 5 | 3 | 3 | 3 | 3 | 3 | 3 | 3 |
| CQ (wt. pts.) | 0.05 | 0.1 | 0.3 | 1 | 1.5 | – | 3 | 4 |
| Ratio for Formulation dQ/TMDPO | 0.01 | 0.03 | 0.10 | 0.33 | 0.50 | 0.00 | 1.00 | 1.33 |
| Tensile Bonding Strength (unit: MPa) | | | | | | | | |
| After 24 hours at 37° C. | | | | | | | | |
| Enamel | 22.3 | 22.0 | 22.5 | 22.3 | 22.1 | 20.8 | 21.4 | 22.9 |
| Dentin | 20.2 | 20.3 | 20.7 | 20.1 | 20.5 | 19.8 | 19.7 | 19.4 |

TABLE 8-continued

|  | Ex. 22 | Ex. 23 | Ex. 24 | Ex. 25 | Ex. 26 | Comp. Ex. 27 | Comp. Ex. 28 | Comp. Ex. 29 |
|---|---|---|---|---|---|---|---|---|
| After Heat Cycle Test | | | | | | | | |
| Enamel | 22.1 | 21.8 | 21.5 | 21.8 | 21.7 | 13.8 | 20.7 | 21.6 |
| Dentin | 20.4 | 20.7 | 20.7 | 20.4 | 21.0 | 13.9 | 19.8 | 20.6 |
| Light Stability (1000 luxes) | | | | | | | | |
| Time before Gelling | >3 min. | >3 min. | >3 min. | >3 min. | >3 min. | >3 min. | 2 min. and 30 sec | 2 min. and 10 sec |

As in Table 8, the bonding agents where the ratio of TMDPO to CQ falls between 1:0.01 and 1:0.5 had excellent bonding durability to tooth. For their light stability, the bonding agents did not gel after exposed to light of 1000 luxes for 3 minutes or longer (Examples 22 to 26). However, the bonding agent not containing CQ had poor bonding durability, though its light stability was good (Comparative Example 27). The bonding agents where the ratio of TMDPO:CQ is 1:1 (Comparative Example 28) or 1:1.33 (Comparative Example 29) gelled after exposed to light of 1000 luxes within 3 minutes, though their bonding strength was high. The data indicate that the light stability of these comparative components is poor.

As described hereinabove, the bonding compositions for dental use of the present invention can firmly bond a tooth and a restorative dental material applied thereto, and, in addition, can kill bacteria remaining in the fine structure of the bonded interface such as toothal canals, etc. Moreover, they can kill bacteria that may penetrate into the bonded interface, and are therefore effective for preventing secondary caries and infectious odontitis.

In the adhesive compositions for dental use of the invention comprising a primer and a bonding agent, the bonding agent comprises an acylphosphine oxide compound and an α-diketone compound both serving as a photopolymerization initiator. In these, not only the bonding agent but also the adhesive primer can be firmly photo-cured at the same time within a short period of time, and the bonding durability of the compositions to the tooth is significantly increased.

Obviously, numerous modifications and variations of the present invention are possible in light of the above teachings. It is therefore to be understood that within the scope of the appended claims, the invention may be practiced otherwise than as specifically described herein.

This application is based on Japanese Patent Application Serial No. JP 10-233777, filed on Aug. 20, 1998, and Japanese Patent Application Serial No. JP 11-17826, filed on Jan. 27, 1999, both of which are incorporated herein by reference in their entirety.

What is claimed is:

1. An adhesive composition, comprising:
    (P) an adhesive primer comprising (i) a polymerizable monomer containing an acid group, (ii) a hydrophilic polymerizable monomer, and (iii) water; and
    (Q) a bonding agent comprising (i) a polymerizable monomer, (ii) an acylphosphine oxide compound, and (iii) an α-diketone compound;
    wherein the ratio of the acylphosphine oxide compound to the α-diketone compound is 1:0.01 to 1:0.5 and the total amount of the acylphosphine oxide compound and the α-diketone compound in the bonding agent is between 1% by weight and 6% by weight.

2. The adhesive composition of claim 1, wherein said bonding agent (Q) further comprises a polymerizable monomer containing an acid group.

3. The adhesive composition of claim 1, wherein said adhesive primer (P) further comprises a polymerization initiator.

4. The adhesive composition of claim 1, wherein the polymerizable monomer (i) of said adhesive primer (P) comprises an acid group comprising phosphoric acid, pyrophosphoric acid, thiophosphoric acid, carboxylic acid, or sulfonic acid.

5. The adhesive composition of claim 4, wherein said polymerizable monomer (i) of said adhesive primer (P) comprises 0.1 to 80% by wt. of said adhesive primer (P).

6. The adhesive composition of claim 1, wherein the acylphosphine oxide compound (ii) of the bonding agent (Q) comprises 2,4,6-trimethylbenzoyldiphenylphosphine oxide, 2,6-diethylbenzoyldiphenylphosphine oxide, 2,6-dimethoxybenzoyldiphenylphosphine oxide, 2,6-dichlorobenzoyldiphenylphosphine oxide, 2,3,5,6-tetramethylbenzoyldiphenylphosphine oxide, benzoyldi-(2,6-dimethylphenyl)phosphonate, 2,4,6-trimethylbenzoyl-ethoxyphenylphosphine oxide or water-soluble acylphosphine oxides.

7. The adhesive composition of claim 1, wherein said α-diketone compound (iii) of said bonding agent (Q) comprises camphorquinone, benzil or 2,3-pentanedione.

8. The adhesive composition of claim 1, wherein said bonding agent (Q) further comprises a reducing agent in an amount of about 0.5 to 10% by wt. based on the total weight of the bonding agent.

9. The adhesive composition of claim 8, wherein said reducing agent comprises amines, aldehydes, mercaptans or salts of sulfinic acids.

10. The adhesive composition of claim 1, wherein according to a light stability test, when 0.03 g of said bonding agent is exposed to a fluorescent lamp at an illuminance of 1,000 luxes, the time before a part of the bonding agent is cured or gelled is greater than 3 minutes.

* * * * *